(12) United States Patent
Dershem

(10) Patent No.: US 8,541,531 B2
(45) Date of Patent: Sep. 24, 2013

(54) ANTI-BLEED COMPOUNDS, COMPOSITIONS AND METHODS FOR USE THEREOF

(75) Inventor: Stephen M Dershem, San Diego, CA (US)

(73) Assignee: Designer Molecules, Inc.

( * ) Notice: Subject to any disclaimer, the term of this patent is extended or adjusted under 35 U.S.C. 154(b) by 273 days.

(21) Appl. No.: 12/933,867

(22) PCT Filed: Mar. 23, 2009

(86) PCT No.: PCT/US2009/037936
§ 371 (c)(1),
(2), (4) Date: Sep. 21, 2010

(87) PCT Pub. No.: WO2009/117729
PCT Pub. Date: Sep. 24, 2009

(65) Prior Publication Data
US 2011/0017400 A1    Jan. 27, 2011

Related U.S. Application Data

(60) Provisional application No. 61/038,728, filed on Mar. 21, 2008.

(51) Int. Cl.
*C08G 77/14*    (2006.01)
(52) U.S. Cl.
USPC ............................. 528/26; 528/27
(58) Field of Classification Search
None
See application file for complete search history.

(56) References Cited

U.S. PATENT DOCUMENTS

| | | | |
|---|---|---|---|
| 4,483,898 A | 11/1984 | Schonhorn et al. | |
| 4,658,049 A | 4/1987 | Nakano et al. | |
| 4,968,738 A | 11/1990 | Dershem | |
| 5,045,127 A | 9/1991 | Dershem et al. | |
| 5,064,480 A | 11/1991 | Dershem et al. | |
| 5,232,962 A | 8/1993 | Dershem et al. | |
| 5,306,333 A | 4/1994 | Dershem et al. | |
| 5,308,525 A * | 5/1994 | Koboyashi et al. | 252/78.3 |
| 5,358,992 A | 10/1994 | Dershem et al. | |
| 5,403,389 A | 4/1995 | Dershem | |
| 5,447,988 A | 9/1995 | Dershem et al. | |
| 5,489,641 A | 2/1996 | Dershem | |
| 5,646,241 A | 7/1997 | Dershem et al. | |
| 5,714,086 A | 2/1998 | Osuna et al. | |
| 5,717,034 A | 2/1998 | Dershem et al. | |
| 5,718,941 A | 2/1998 | Dershem et al. | |
| 5,753,748 A | 5/1998 | Dershem et al. | |
| 5,861,111 A | 1/1999 | Dershem et al. | |
| 5,969,036 A | 10/1999 | Dershem | |
| 5,973,166 A | 10/1999 | Mizori et al. | |
| 6,034,194 A | 3/2000 | Dershem | |
| 6,034,195 A | 3/2000 | Dershem | |
| 6,048,953 A | 4/2000 | Kawashima et al. | |
| 6,121,358 A | 9/2000 | Dershem et al. | |
| 6,187,886 B1 | 2/2001 | Husson, Jr. et al. | |
| 6,211,320 B1 | 4/2001 | Dershem et al. | |
| 6,423,780 B1 | 7/2002 | Dershem et al. | |
| 6,429,281 B1 | 8/2002 | Dershem et al. | |
| 6,521,731 B2 | 2/2003 | Dershem et al. | |
| 6,576,734 B1 * | 6/2003 | Matsuo et al. | 528/25 |
| 6,620,946 B2 | 9/2003 | Dersehm et al. | |
| 6,743,852 B2 | 6/2004 | Dershem et al. | |
| 6,750,301 B1 | 6/2004 | Bonneau et al. | |
| 6,790,597 B2 | 9/2004 | Dershem | |
| 6,825,245 B2 | 11/2004 | Dershem | |
| 6,831,132 B2 | 12/2004 | Liu et al. | |
| 6,852,814 B2 | 2/2005 | Dershem et al. | |
| 6,916,856 B2 | 7/2005 | Dershem | |
| 6,946,523 B2 | 9/2005 | Dershem et al. | |
| 6,960,636 B2 | 11/2005 | Dershem et al. | |
| 6,963,001 B2 | 11/2005 | Dershem et al. | |
| 7,102,015 B2 | 9/2006 | Dershem et al. | |
| 7,157,587 B2 | 1/2007 | Mizori et al. | |
| 7,176,044 B2 | 2/2007 | Forray et al. | |
| 7,199,249 B2 | 4/2007 | Liu et al. | |
| 7,208,566 B2 | 4/2007 | Mizori et al. | |
| 7,285,613 B2 | 10/2007 | Dershem et al. | |
| 7,309,724 B2 | 12/2007 | Dershem et al. | |
| 7,316,846 B2 * | 1/2008 | Cheng et al. | 428/447 |
| 7,517,925 B2 | 4/2009 | Dershem et al. | |
| 7,678,879 B2 | 3/2010 | Dershem | |
| 7,777,064 B2 | 8/2010 | Mizori | |
| 7,786,234 B2 | 8/2010 | Dershem et al. | |
| 7,786,248 B2 | 8/2010 | Dershem | |
| 7,795,362 B2 | 9/2010 | Dershem | |
| 7,868,113 B2 | 1/2011 | Dershem | |
| 7,875,688 B2 | 1/2011 | Dershem et al. | |
| 7,884,174 B2 | 2/2011 | Mizori et al. | |
| 7,928,153 B2 | 4/2011 | Dershem | |
| 8,008,419 B2 | 8/2011 | Dershem | |

(Continued)

FOREIGN PATENT DOCUMENTS

| | | | |
|---|---|---|---|
| EP | 1834969 | | 9/2007 |
| EP | 1900785 | * | 3/2008 |

(Continued)

OTHER PUBLICATIONS

International Search Report for PCT/US09/37936, 1-3, 2009.

(Continued)

*Primary Examiner* — Marc Zimmer
(74) *Attorney, Agent, or Firm* — The Law Office of Jane K. Babin, Professional Corporation; Jane K. Babin

(57) ABSTRACT

The invention is based on the discovery that addition of certain carboxylic acid derivatives of siloxanes to thermosetting adhesive compositions and die-attach pastes renders such compositions and pastes extremely resistant to resin bleed. The present invention provides siloxane-carboxylic acid compounds useful as anti-bleed additives. Also provided are adhesive compositions and pastes containing the compounds of the invention, which are particularly useful in applications that require little to no resin bleed prior to curing of the compositions (such as e.g., electronic packaging applications).

17 Claims, 6 Drawing Sheets

(56) References Cited

U.S. PATENT DOCUMENTS

| | | |
|---|---|---|
| 8,013,104 B2 | 9/2011 | Dershem |
| 8,039,663 B2 | 10/2011 | Dershem |
| 8,043,534 B2 | 10/2011 | Dershem |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0199638 A1 | 10/2003 | Liu et al. |
| 2003/0208016 A1 | 11/2003 | Dershem et al. |
| 2004/0006166 A1 | 1/2004 | Liu et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0107542 A1 | 5/2005 | Liu et al. |
| 2005/0136620 A1 | 6/2005 | Dershem et al. |
| 2005/0137277 A1 | 6/2005 | Dershem et al. |
| 2005/0267254 A1 | 12/2005 | Mizori et al. |
| 2005/0272888 A1 | 12/2005 | Dershem et al. |
| 2006/0009570 A1 | 1/2006 | Zychowski |
| 2006/0009578 A1 | 1/2006 | Dershem |
| 2006/0063014 A1 | 3/2006 | Forray |
| 2006/0069232 A1 | 3/2006 | Dershem |
| 2006/0142517 A1 | 6/2006 | Dershem |
| 2007/0042173 A1 | 2/2007 | Nagaoka et al. |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dersham |
| 2008/0257493 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |
| 2010/0113643 A1 | 5/2010 | Dershem |
| 2010/0144977 A1 | 6/2010 | Dershem |
| 2010/0249276 A1 | 9/2010 | Dershem |
| 2011/0017400 A1 | 1/2011 | Dershem |
| 2011/0152466 A1 | 6/2011 | Dershem |

FOREIGN PATENT DOCUMENTS

| | | |
|---|---|---|
| JP | 11246759 | 9/1999 |
| JP | H10-505599 | 9/2007 |
| WO | WO-9607691 | 3/1996 |
| WO | WO 2004/099331 | 11/2004 |
| WO | WO-2004099331 | 11/2004 |
| WO | WO-2005121190 | 12/2005 |
| WO | WO-2007100329 | 9/2007 |
| WO | WO-2008077140 | 6/2008 |
| WO | WO-2008077141 | 6/2008 |
| WO | WO-2008092168 | 7/2008 |
| WO | WO-2008124797 | 10/2008 |
| WO | WO-2008130894 | 10/2008 |
| WO | WO-2009117729 A2 | 9/2009 |
| WO | WO-2009117729 A3 | 9/2009 |
| WO | WO-2010019832 A2 | 2/2010 |

OTHER PUBLICATIONS

Ganapathy et al., "Ring-opening polymerization of-lactide in supercritical carbon dioxide using PDMS based stabilizers.", European Polymer Journal 43:119-126, Jan. 2007.

Lim et al., "Synthesis and characterization of Poly (dimethyl siloxane)- Poly[alkyl (meth)acrylic acid] Block Copolymers", Macromolecules 32:2811-2815, 1992.

* cited by examiner 0.05% anti-bleed

ANTI-BLEED COMPOUNDS, COMPOSITIONS AND METHODS FOR USE THEREOF

RELATED APPLICATIONS

This application is the U.S. National Stage under 35 USC §371 of PCT/US09/037936 (filed Mar. 23, 2009); which in turn claims the benefit of priority under 35 USC §119 of U.S. Provisional Applications Ser. No. 61/038,728 filed Mar. 21, 2008, the entire disclosures of which are incorporated herein by reference.

FIELD OF THE INVENTION

The present invention relates to adhesive compositions, methods of preparation and uses therefore. In particular, the invention relates to additives used in adhesive compositions including compounds that reduce resin bleed upon application to a substrate and prior to cure.

BACKGROUND OF THE INVENTION

Adhesives used in the electronic packaging industry typically contain a thermosetting resin combined with a filler and some type of curing initiator. These resins are primarily used in the electronics industry for the preparation of non-hermetic electronic packages. Adhesives useful for electronic packaging applications typically exhibit properties such as good mechanical strength, curing properties that do not affect the component or the carrier, and rheological properties compatible with application to microelectronic and semiconductor components. Examples of such packages are ball grid array (BGA) assemblies, super ball grid arrays, IC memory cards, chip carriers, hybrid circuits, chip-on-board, multi-chip modules, pin grid arrays, and the like. For all these applications, the microelectronics industry continues to require new resins that are able to meet its varying demands.

Monomer components used in adhesive die attach paste compositions tend to bleed out onto the substrate during cure, and even (in some cases) during room temperature staging of the adhesive. Indeed, resin bleed can be a serious problem in die attach electronic packaging applications. "Bleed" is defined herein as separation of the monomer vehicle phase and filler during staging or cure, resulting in the spread of resin away from the die bond area. Resin bleed can generate wire bond non-sticks if it flows up onto bonding pads of the microelectronic device itself or the package into which it has been placed.

There are several potential consequences that arise due to resin bleed, e.g., a package assembler must deal with the likelihood of reduced product yields (and the attendant increased costs for manufacture), the part-to-part variability of the bleed phenomenon results in unacceptable part-to-part variability of the desired product, thereby necessitating the additional expense of 100% visual inspection of each component before being passed onto the wire bond step, and the like.

U.S. Pat. No. 4,483,898 discloses the use of alcohols, amides, amines, carboxylic acids, and esters containing two to twelve carbon atoms as being effective for the reduction of spreading of liquid films on substrates, specifically in inhibition of resin bleed for epoxy, acrylate and silicone adhesive systems. The preferred bleed inhibiting compounds were poly-fluorinated (i.e. where most or all of the hydrogens of the hydrocarbon residue had been replaced by fluorine). The effective range contemplated by this patent is 0.05 to 5% by weight of the liquid phase. It is interesting to note, however, that the bleed control failed at 0.2% by weight of the most preferred bleed inhibiting agent in the absence of any "coupling agent" (cf. example VII). Furthermore, several of the compounds disclosed had deleterious effects on the pot life of the epoxy systems in which they were used. Another serious concern connected to the previously disclosed anti-bleed additives is their potential human and environmental toxicity. Poly-fluorinated hydrocarbons, with more than about four carbons in the backbone, are known to bio-accumulate (i.e. to become concentrated in living organisms, and no naturally occurring biological mechanisms exist that can eliminate these compounds from the body once they are absorbed). These materials, therefore, are considered to pose a risk to personal health as well as to the environment.

Accordingly, there remains a need to develop environmentally friendly compounds, compositions and methods useful for reducing the occurrence of resin bleed when die-attach compositions are applied to a substrate.

SUMMARY OF THE INVENTION

The present invention provides carboxylate salt and carboxylic acid terminated siloxane anti-bleed compounds, adhesive compositions (including die-attach pastes) containing the anti-bleed compounds, and methods for adhering members, such as semiconductor dies, using the same. The anti-bleed compounds of the invention render such adhesive compositions and die-attach pastes extremely resistant to resin bleed and useful as biologically and ecologically benign anti-bleed agents.

Specifically, the present invention provides compounds having the formulae:

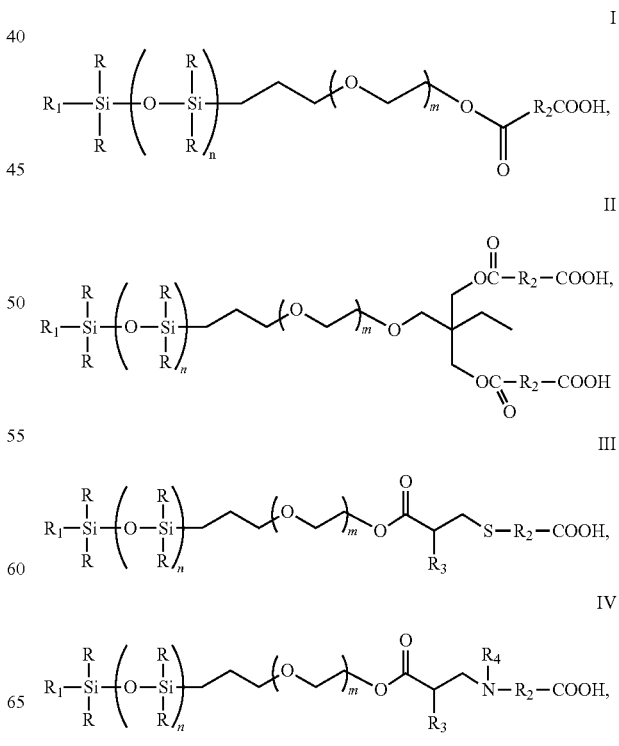

-continued

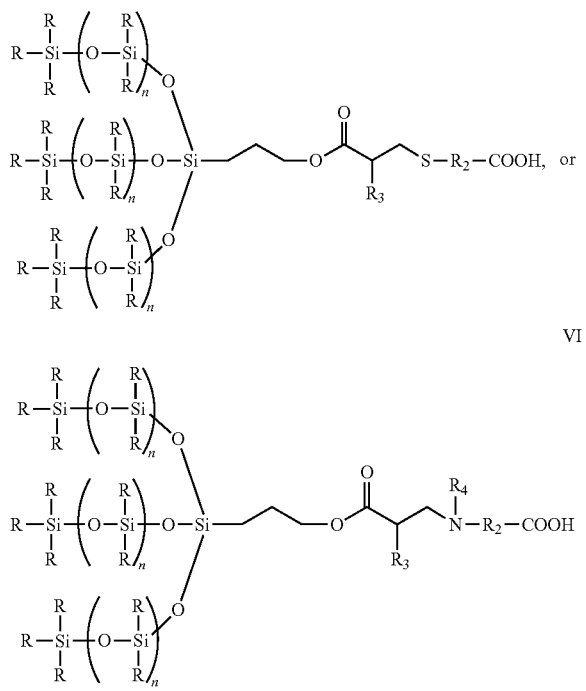

where each R and $R_1$ is independently $C_1$ to $C_8$ alkyl or phenyl, $R_2$ is selected from straight or branched chain alkyl, substituted alkyl, alkenyl, substituted alkenyl, alkynyl, substituted alkynyl, cycloalkyl, substituted cycloalkyl, aromatic, substituted aromatic, heterocyclic, substituted heterocyclic, heteroaromatic, or substituted heteroaromatic, $R_3$ is hydrogen or methyl, is selected from straight or branched chain alkyl, substituted alkyl, aromatic, or substituted aromatic, n is 3 to 500, and m is 0 to 100.

In other embodiments, R2 can be optionally substituted methyl, ethyl, ethenyl, methylethenyl, n-propyl, isopropyl, propenyl, butyl, isobutyl, sec-butyl, tert-butyl, butenyl, pentyl, pentenyl, hexyl, hexenyl, octyl, or octenyl; ethylallyl, ethyloctenyl, ethyldodecenyl, ethyloctadecenyl, cyclohexane, cyclohexene, bicyclohexane, norbornenyl, phenyl, or naphthyl.

In other embodiments, $R_2$ has the formula $(CH_2)_m R_5 (R_6)_m$, where $R_5$ is a heteroatom, $R_6$ is optionally substituted alkyl, and each m is independently 1-12.

In certain embodiments of the invention, R is methyl. In certain aspects $R_1$ is butyl. In some embodiments of the invention R is methyl and $R_1$ is butyl.

In yet further embodiments, $R_2$ is $C_4$-$C_{12}$ straight or branched chain alkyl, substituted alkyl, alkenyl, substituted alkenyl, alkynyl, substituted alkynyl, cycloalkyl, substituted cycloalkyl, heterocyclic, substituted heterocyclic, heteroaromatic, or substituted heteroaromatic, and n is at least about 10 to at least about 250. In some aspects of the invention, $R_2$ comprises at least one vinyl group.

Exemplary compounds of formula I according to the present invention include:

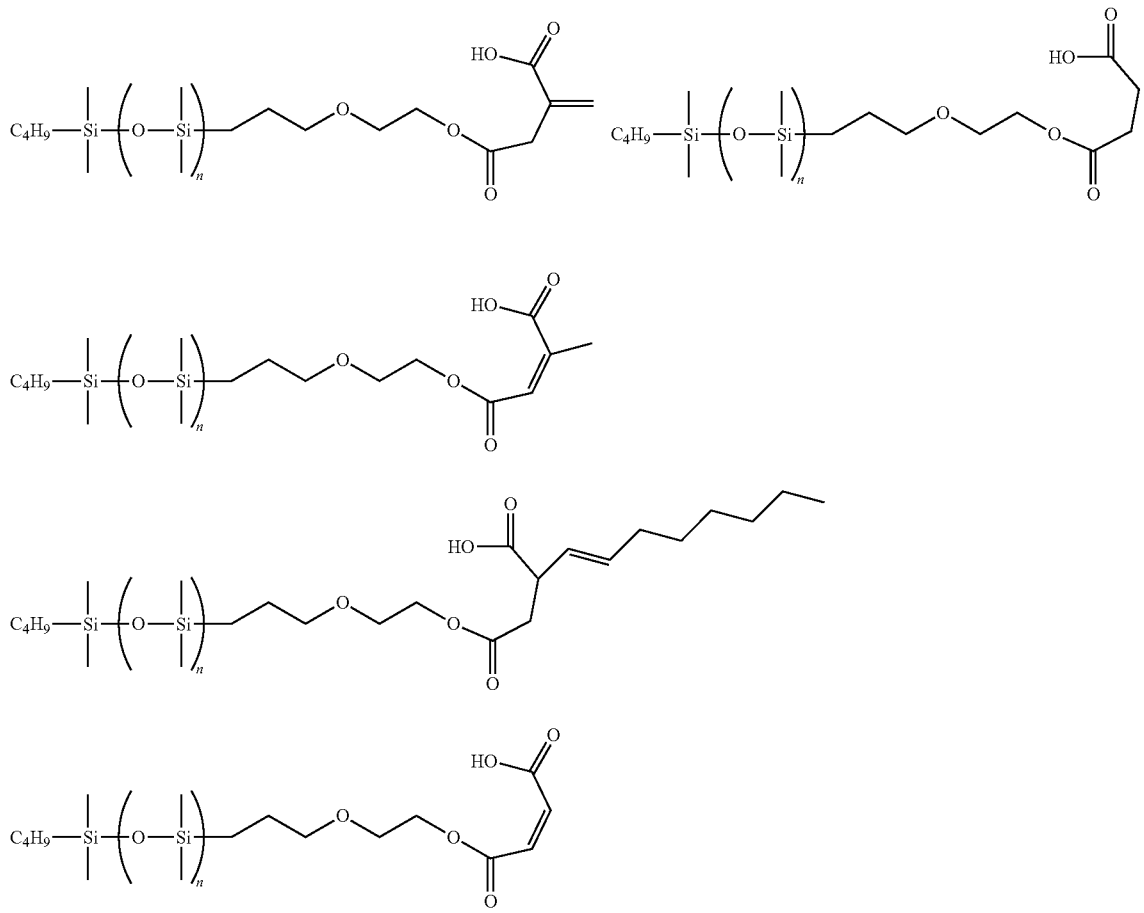

-continued
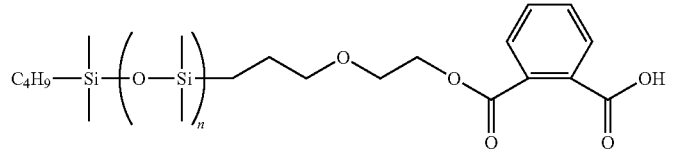
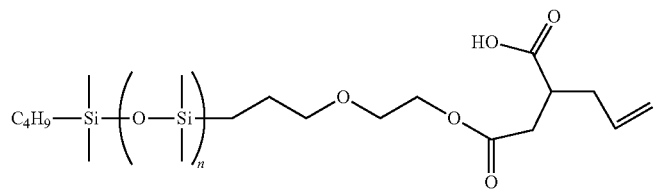
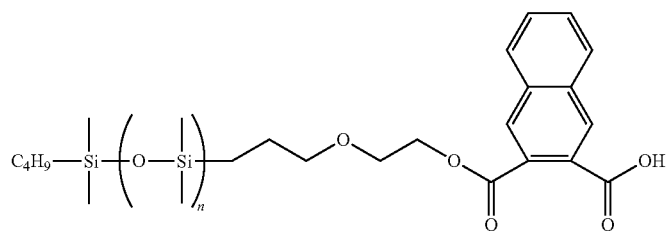
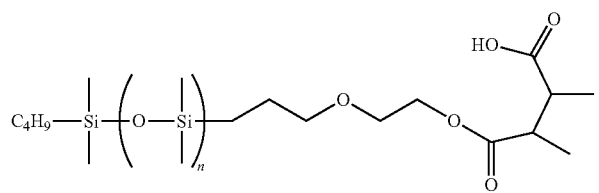
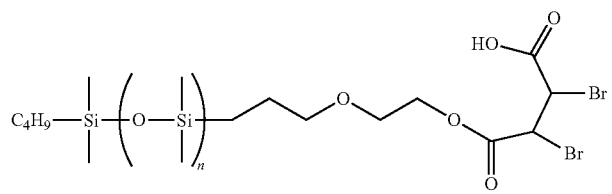
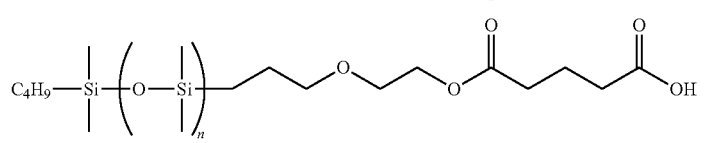
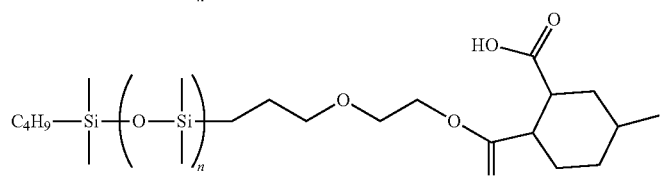
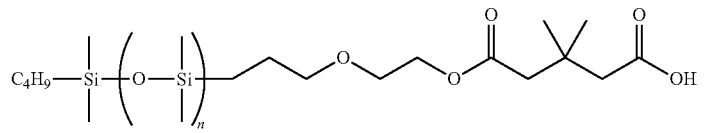
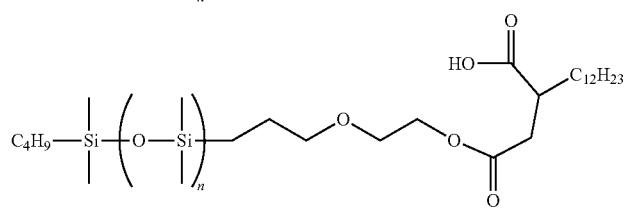

-continued
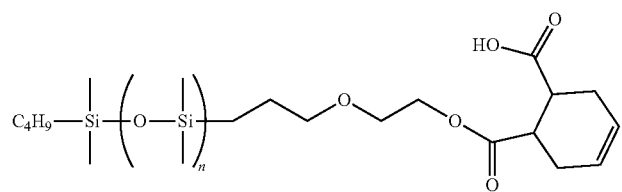
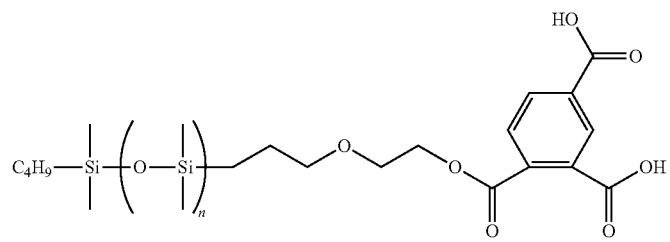
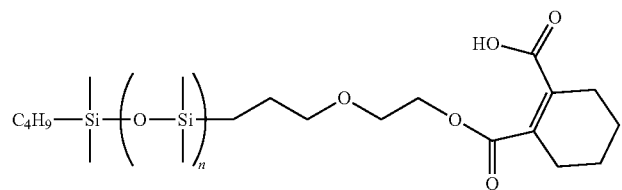
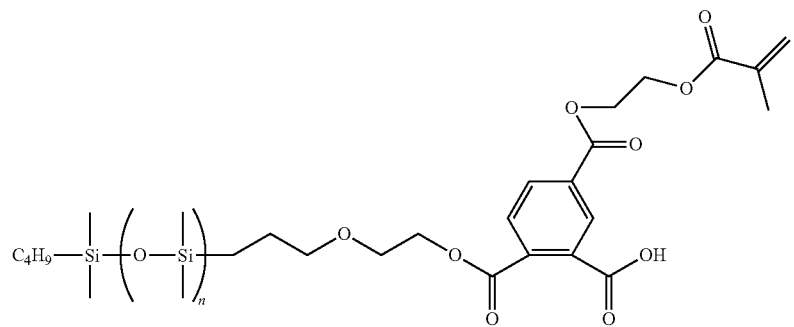
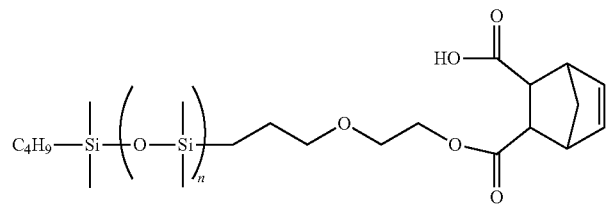
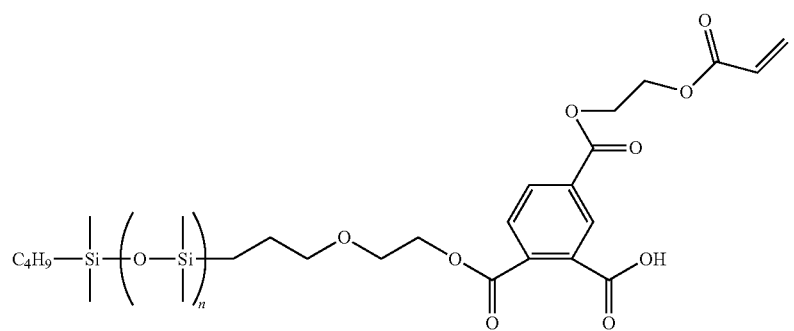

Also provided by the invention is compound having the formula:

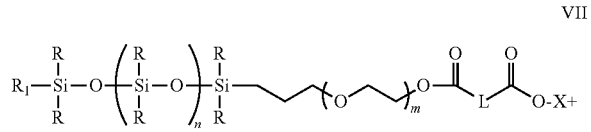

where each R and $R_1$ is independently $C_1$ to $C_8$ alkyl or phenyl; X is a cation; L is $C_2$ to $C_{10}$ alkyl, alkenyl, cycloalkyl, cycloalkenyl, aryl, naphthyl; n is to 500 and m is 0 to 100, and the X cation is selected from ammonium, alkyl ammonium, dialkyl ammonium, trialkyl ammonium, tetraalkyl ammonium, cycloalkyl ammonium, aryl ammonium, substituted aryl ammonium, pyridinium, substituted pyridinium, or a mono-valent or poly-valent metal cation selected from lithium, sodium, potassium, cesium, magnesium, calcium, strontium, barium, copper, zinc, aluminum, tin, or bismuth.

Exemplary compounds of formula VII according to the present invention include:

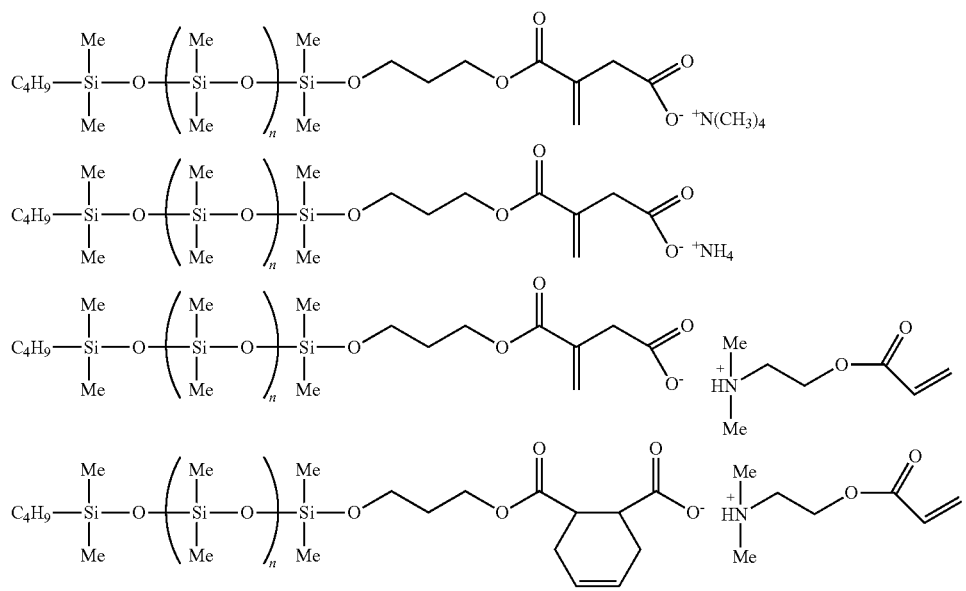

The present invention also provides adhesive compositions containing a thermosetting resin, a quantity of the anti-bleed agent of any one of formulae I-VII sufficient to reduce resin bleed upon application of the adhesive composition to a substrate, and at least one curing initiator.

According to this embodiment of the invention, the thermosetting resin can be selected from epoxies, oxetanes, oxazolines, benzoxazines, resoles, maleimides, cyanate esters, acrylates, methacrylates, maleates, fumarates, itaconates, vinyl esters, vinyl ethers, cyanoacrylates, or styrenics or combinations thereof. In certain embodiments, the anti-bleed agent comprises about 0.01 to about 5.0 weight percent of the total composition.

The present invention also provides die-attach paste adhesive compositions containing a) 2 weight percent to about 98 weight percent (wt %) of a thermosetting resin; b) a quantity of an anti-bleed agent of formula I and/or formula II sufficient to reduce resin bleed upon application of the die-attach paste to a substrate; c) 0 to about 90 wt % of a filler; d) 0.1 wt % to about 5 wt % of at least one curing initiator, based on total weight of the paste; e) 0.1 wt % to about 4 wt %, of at least one coupling agent, based on total weight of the paste.

Also provided by the present invention are methods for attaching a first article to a second article, including the steps of a) applying an adhesive composition of the invention to the first article; b) bringing the first and the second article into contact to form an assembly wherein the first article and the second article are separated only by the adhesive composition applied in a); and thereafter, c) subjecting the assembly to conditions suitable to cure the invention adhesive composition. According to the present invention, the first and second articles can be reversibly attached.

In yet another method of the invention, a first semiconductor die is attached to a second semiconductor die, by following the steps of: a) providing a first die having a topside and an underside; b) applying a die-attach paste of the invention to the underside of the first die; c) juxtaposing the first die and the second die such that the die-attach paste is an interface between the underside of the first die and the topside of the second die; and d) curing the die-attach paste, thereby attaching a first semiconductor die to a second semiconductor die.

DETAILED DESCRIPTION OF THE INVENTION

Figure 1:
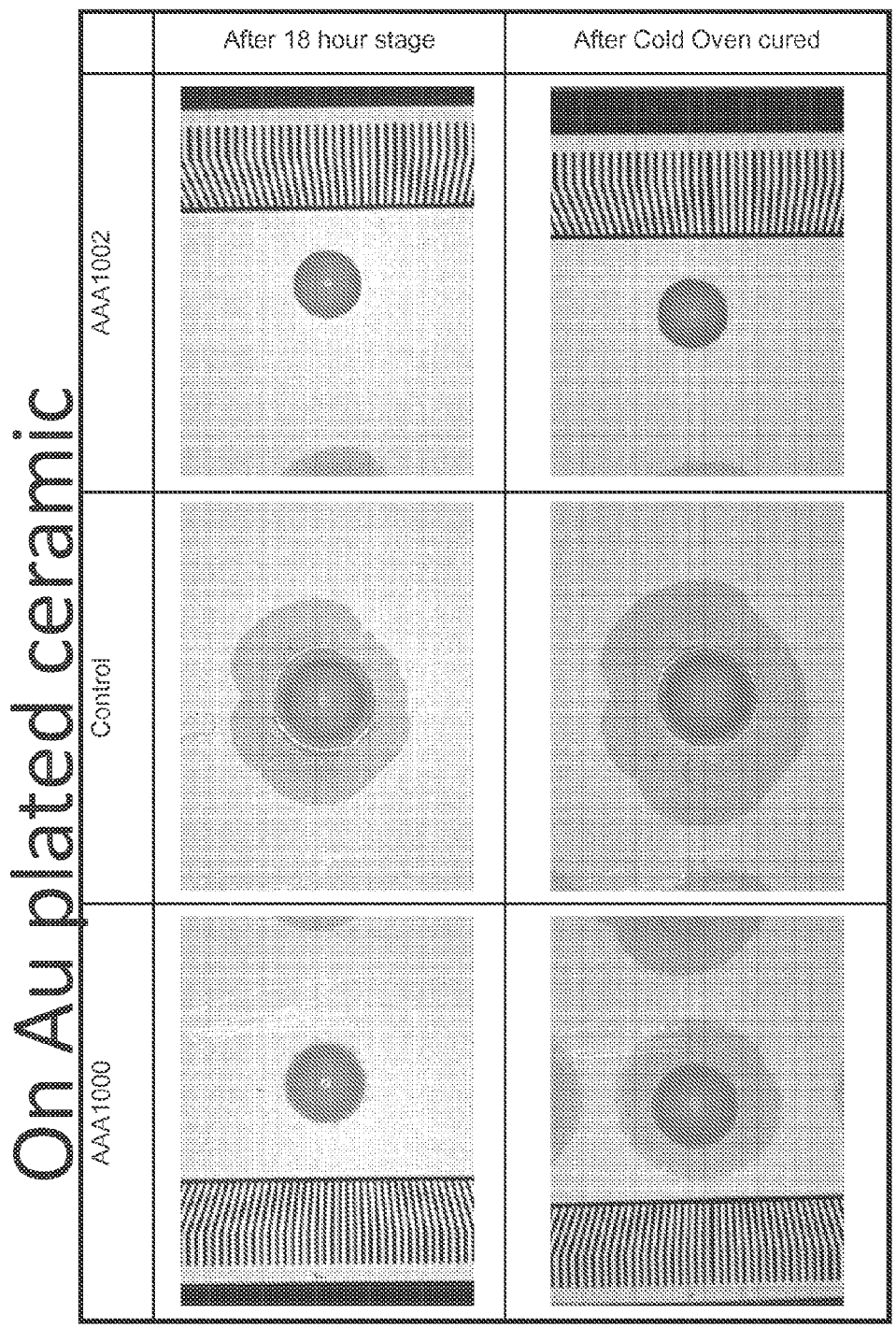
FIG. 1 shows a comparison of resin bleed from a die-attach paste with and without an anti-bleed agent of the invention.

Unless specific definitions are provided, the nomenclatures utilized in connection with, and the laboratory procedures and techniques of analytical chemistry, synthetic organic and inorganic chemistry described herein are those known in the art. Standard chemical symbols are used interchangeably with the full names represented by such symbols. Thus, for example, the terms "hydrogen" and "H" are understood to have identical meaning Standard techniques may be used for chemical syntheses, chemical analyses, and formulation. The foregoing techniques and procedures can be generally performed according to conventional methods well known in the art.

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described.

Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated).

"About" as used herein means that a number referred to as "about" comprises the recited number plus or minus 1-10% of that recited number. For example, "about" 100 degrees can mean 95-105 degrees or as few as 99-101 degrees depending on the situation. Whenever it appears herein, a numerical range such as "1 to 20" refers to each integer in the given range; e.g., "1 to 20 carbon atoms" means that an alkyl group can contain only 1 carbon atom, 2 carbon atoms, 3 carbon atoms, etc., up to and including 20 carbon atoms, although the term "alkyl" also includes instances where no numerical range of carbon atoms is designated).

"Adhesive" or "adhesive compound" as used herein, refers to any substance that can be used to adhere or bonds two items together. Implicit in the definition of an "adhesive composition" or "adhesive formulation" is the fact that the composition or formulation is a combination or mixture of more than one species, component or compound, which can include adhesive monomers, oligomers, and/or polymers along with other materials, whereas an "adhesive compound" refers to a single species, such as an adhesive polymer or oligomer.

More specifically, adhesive composition refers to un-cured mixtures in which the individual components in the mixture retain the chemical and physical characteristics of the individual components of which the mixture is made. Adhesive compositions are typically malleable and may be liquids, paste, gel or another form that can be applied to an item so that is can be bonded to another item.

"Cured adhesive," cured adhesive composition" or "cured adhesive compound" refers to adhesives which have undergone a chemical and/or physical changes such that the mixtures is transformed into a solid, substantially non-flowing material which curing process may involve e.g. crosslinking.

"Curable" means that a compound or composition material can be transformed into a solid, substantially non-flowing material by means of chemical reaction (e.g. Michael addition) crosslinking, radiation crosslinking, or the like. Thus, adhesive compositions of the invention are curable, but unless otherwise specified, are not cured.

The present invention is based on the discovery that the addition of carboxylate salt or carboxylic acid terminated siloxanes to thermosetting adhesive compositions and die-attach pastes renders such compositions and pastes extremely resistant to resin bleed.

"Bleed" or "resin bleed," as used herein, refers to the spread of resin away from a bond area during the process of adhering one object to another. Resin bleed may result from the separation of an adhesive vehicle phase (e.g., monomer) and a filler during staging or cure of the adhesive. In certain embodiments of the invention, the bond area is an electronics die bonded to a substrate.

The present invention thus provides siloxane compounds useful as anti-bleed agents.

The compounds of the invention generally include a hydrophobic and oleophobic polydimethylsiloxane tail terminated with a carboxylic acid or carboxylate. The invention also provides carboxylate salt anti-bleed compounds.

As used herein, "anti-bleed agent" refers to compounds, which, acting alone or in combination, reduce and/or inhibit separation of an adhesive vehicle and filler. The adhesive can, for example, be a thermosetting adhesive containing a monomer vehicle phase and a filler.

"Thermoplastic," as used herein, refers to the ability of a compound, composition or other material (e.g. a plastic) to melt to a liquid when heated and freeze to solid, often brittle and glassy, state when cooled sufficiently.

"Thermoset," as used herein, refers to the ability of a compound, composition or other material to irreversibly "cure" to a stronger, harder form. Thermoset materials are typically polymers that may be cured, for example, through heat (e.g. above 200 degrees Celsius), via a chemical reaction (e.g. epoxy), or through irradiation (e.g. U.V. irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible solid or rubber by a cross-linking process. Thus, energy and/or catalysts are added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

The present invention provides a compound of any one the formulae:

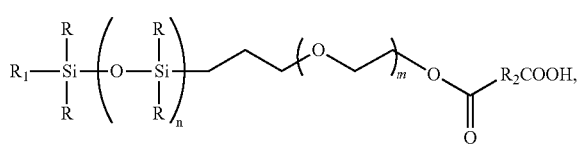

I

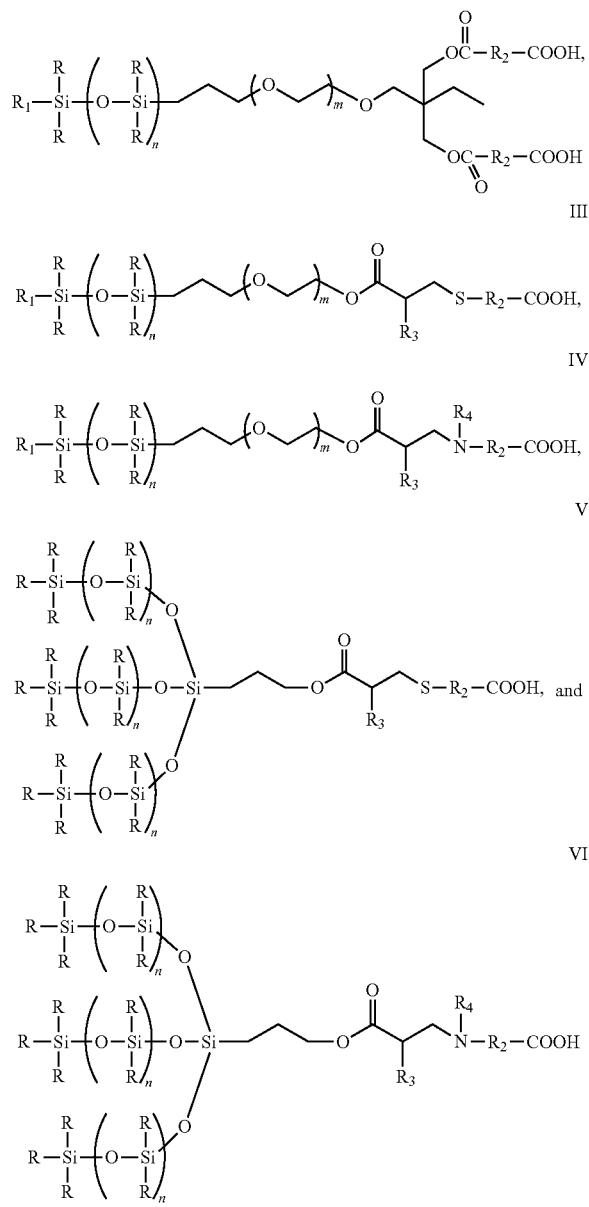

where each R and $R_1$ is independently $C_1$ to $C_8$ alkyl; or phenyl, $R_2$ is selected from straight or branched chain alkyl, substituted alkyl, alkenyl, substituted alkenyl, alkynyl, substituted alkynyl, cycloalkyl, substituted cycloalkyl, aromatic, substituted aromatic, heterocyclic, substituted heterocyclic, heteroaromatic, or substituted heteroaromatic, $R_3$ is H or Me, and $R_4$ is selected from straight or branched chain alkyl, substituted alkyl, aromatic, or substituted aromatic, n is 3 to 500, and m is 0 to 100.

In certain embodiments, R is $C_1$ to $C_6$ alkyl. In other embodiments, R is $C_1$ to $C_4$ alkyl. In yet other embodiments, R is methyl. In certain embodiments, $R_1$ is $C_1$ to $C_6$ alkyl. In other embodiments, $R_1$ is $C_2$ to $C_4$ alkyl. In yet other embodiments, $R_1$ is butyl.

$R_2$ is typically a $C_1$-$C_{50}$, $C_2$-$C_{30}$, $C_2$-$C_{12}$ or $C_2$-$C_8$ alkyl, substituted alkyl, alkenyl, substituted alkenyl, alkynyl, substituted alkynyl, cycloalkyl, substituted cycloalkyl, heterocyclic, substituted heterocyclic, heteroaromatic, or substituted heteroaromatic.

In certain embodiments, is $R_2$ is selected from optionally substituted methyl, ethyl, ethenyl, methylethenyl, n-propyl, isopropyl, propenyl, butyl, isobutyl, sec-butyl, tert-butyl, butenyl, pentyl, pentenyl, hexyl, hexenyl, octyl, or octenyl; ethylallyl, ethyloctenyl, ethyldodecenyl, ethyloctadecenyl, cyclohexane, cyclohexene, bicyclohexene, norbornenyl, phenyl, or naphthyl. In certain other embodiments. $R_2$ is an optionally substituted maleimide, cyclohexane, cyclohexene, bicyclohexene, benzoic acid, In yet another embodiment, $R_2$ has the formula: $(CH_2)_m R_5 (R_6)_m$
where $R_5$ is a heteroatom; $R_6$ is optionally substituted alkyl; and each m is independently 1-12.

In certain aspects to this embodiment, $R_2$ is an optionally substituted $C_2$-$C_4$ amino or sufenyl moiety. In certain embodiments, of the invention, R is methyl. In certain aspects $R_1$ is butyl. In certain other embodiments, R is methyl and $R_1$ is butyl.

In yet further embodiments, $R_2$ is $C_4$-$C_{12}$ straight or branched chain alkyl, substituted alkyl, alkenyl, substituted alkenyl, alkynyl, substituted alkynyl, cycloalkyl, substituted cycloalkyl, heterocyclic, substituted heterocyclic, heteroaromatic, or substituted heteroaromatic, and n is at least about 10 to at least about 250. In certain aspects of the invention, $R_2$ comprises at least one carboxylic acid, vinyl or ester sidechain.

In certain embodiments of the invention, n is at least about 10, at least about 20, at least about 50 or at least about 100. In other embodiments, n is about 10 to about 500, about 20 to about 250, or about 50 to about 100.

In one embodiment, the invention provides a compound of formula I where R is methyl; $R_1$ is $C_1$-$C_6$ alkyl; $R_2$ is $C_4$-$C_{12}$ straight or branched chain alkyl, substituted alkyl, alkenyl, substituted alkenyl, alkynyl, substituted alkynyl, cycloalkyl, substituted cycloalkyl, heterocyclic, substituted heterocyclic, heteroaromatic, or substituted heteroaromatic; and n is at least about 10 to at least about 250.

Exemplary compounds of formula I according to the present invention include:

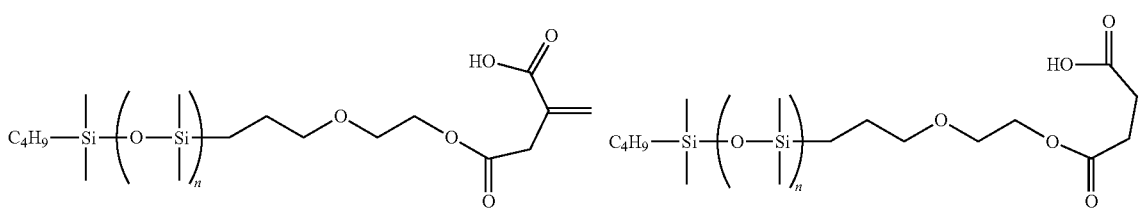

-continued
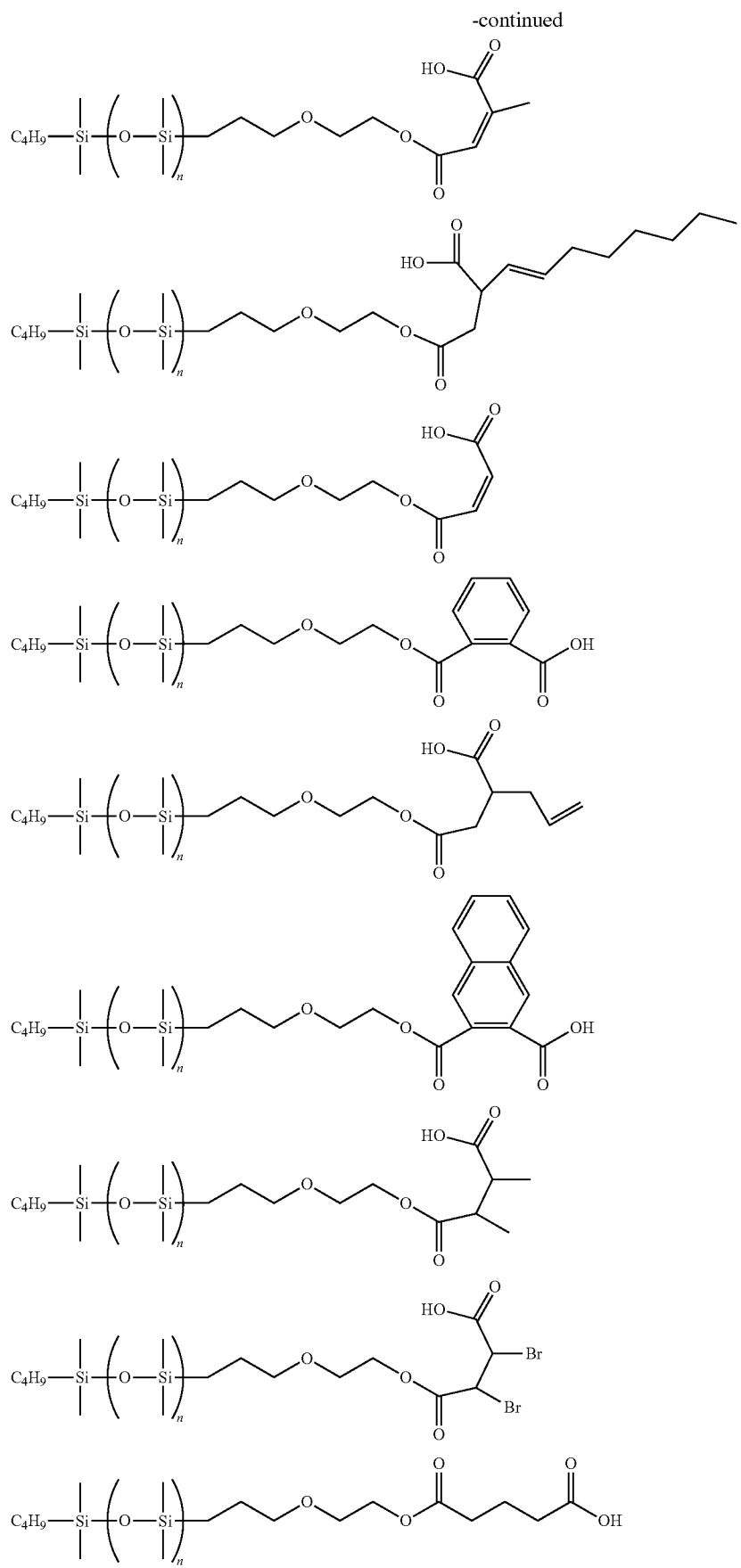

-continued
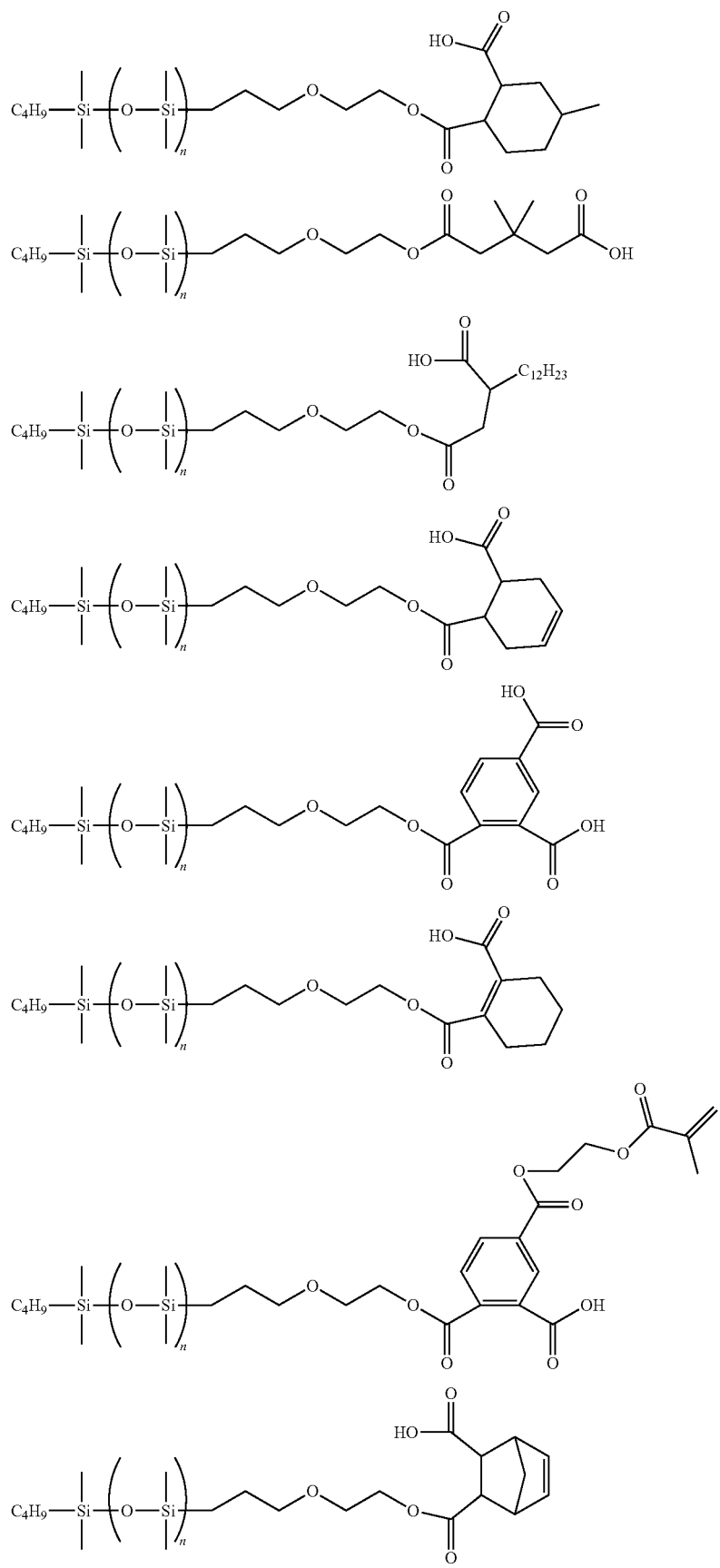

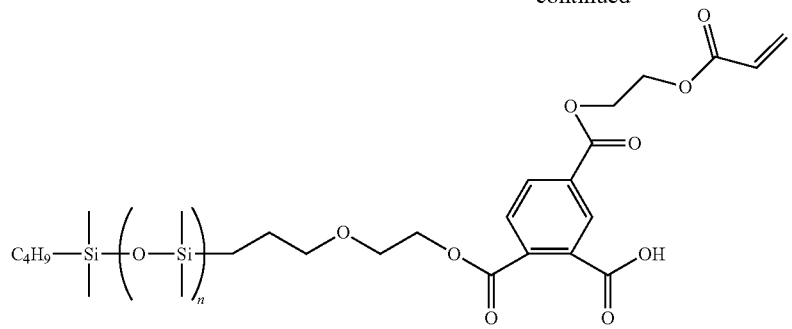

15

Also provided by the invention is compound having the formula:

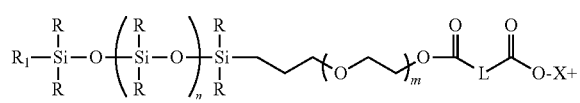

VII where each R and $R_1$ is independently $C_1$ to $C_8$ alkyl or phenyl; X is a cation; L is $C_2$ to $C_{10}$ alkyl, alkenyl, cycloalkyl, cycloalkenyl, aryl, naphthyl; n is to 500 and m is 0 to 100, and the X cation is selected from ammonium, alkyl ammonium, dialkyl ammonium, trialkyl ammonium, tetraalkyl ammonium, cycloalkyl ammonium, aryl ammonium, substituted aryl ammonium, pyridinium, substituted pyridinium, or a mono-valent or poly-valent metal cation selected from lithium, sodium, potassium, cesium, magnesium, calcium, strontium, barium, copper, zinc, aluminum, tin, or bismuth.

Exemplary compounds of formula VII according to the present invention include:

carbon atoms, frequently from 1 to about 12 carbon atoms, and most frequently from 1 to about 8 carbon atoms. Examples of alkyl radicals include methyl, ethyl, n-propyl, isopropyl, n-butyl, isobutyl, sec-butyl, tert-butyl, pentyl, hexyl, octyl and the like. Whenever it appears herein, a numerical range, such as "1 to 500" or "$C_1$-$C_{500}$", refers to each integer in the given range; e.g., "$C_1$-$C_{500}$ alkyl" means that an alkyl group may comprise only 1 carbon atom, 2 carbon atoms, 3 carbon atoms, etc., up to and including 500 carbon atoms, although the term "alkyl" also includes instances where no numerical range of carbon atoms is designated).

"Substituted alkyl" refers to alkyl moieties bearing one or more, typically 1 to 4, and frequently 1 to 2 of the following substituents: alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, arylalkyl, alkylamino, dialkylamino, substituted aryloxy, halogen (e.g. F, Cl, Br, I), haloalkyl, cyano, nitro, nitrone, amino, amido, —C(O)H,

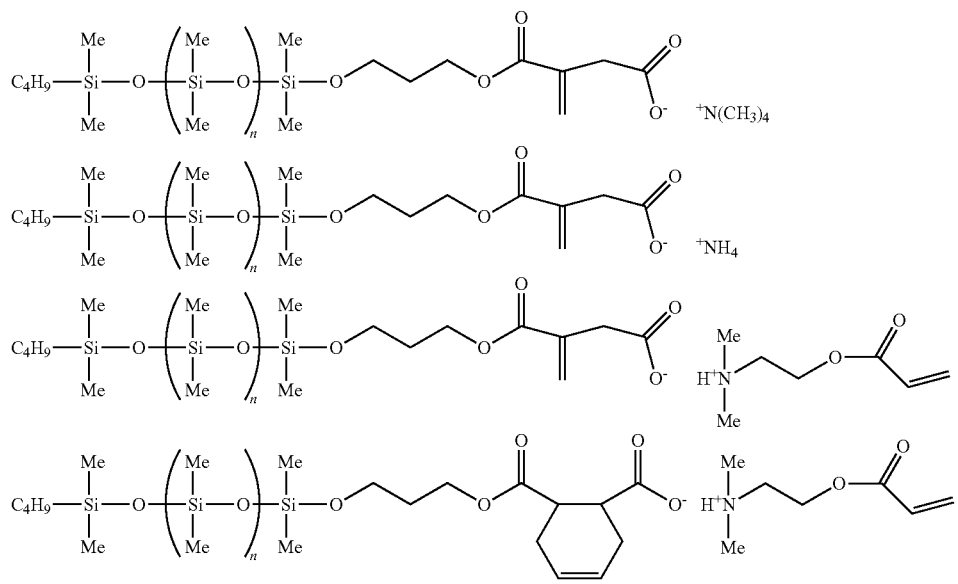

The term "alkyl" refers to an optionally substituted straight-chain or branched-chain hydrocarbon radical having from 1 to about 50 carbon atoms, typically from 1 to about 20

—C(O)—, —C(O)O—, —S—, —S(O)$_2$, —OC(O)—O—, —NR—C(O), —NR—C(O)—NR, —OC(O)—NR, wherein R is H or lower alkyl, acyl, oxyacyl, carboxyl, carbamate, sulfonyl, sulfonamide, sulfuryl, and the like. As used herein, "lower alkyl" refers to alkyl moieties having from 1 to about 12 carbon atoms.

The term "alkenyl" refers to a straight-chain or branched-chain hydrocarbon radical having one or more carbon-carbon double-bonds and having from 2 to about 50 carbon atoms, typically from 2 to about 20 carbon atoms, frequently from 2 to about 12 carbon atoms, and most frequently from 2 to about 8 carbon atoms. Examples of alkenyl radicals include ethenyl, propenyl, 1,4-butadienyl and the like. "Substituted alkenyl" refers to alkenyl groups further bearing one or more substituents as set forth above.

The term "alkynyl" refers to a straight-chain or branched-chain hydrocarbon radical having one or more carbon-carbon triple-bonds and having from 2 to about 12 carbon atoms. Examples of alkynyl radicals include ethynyl, propynyl, butynyl and the like. "Substituted alkynyl" refers to alkynyl groups further bearing one or more substituents as set forth above.

The term "aryl" refers to optionally substituted aromatic ring systems, typically having in the range of 6 to about 14 carbon atoms and "substituted aryl" refers to aryl groups further bearing one or more substituents as set forth above. The term aryl includes monocyclic aromatic rings, polycyclic aromatic ring systems, and polyaromatic ring systems. The polyaromatic and polycyclic ring systems may contain from two to four, more preferably two to three, and most preferably two, rings. In some embodiments, aryl groups contain 5- or 6-membered aromatic ring systems.

As used herein, "alkylaryl" refers to alkyl-substituted aryl groups and "substituted alkylaryl" refers to alkylaryl groups further bearing one or more substituents as set forth above.

As used herein, "arylalkyl" refers to aryl-substituted alkyl groups and "substituted arylalkyl" refers to arylalkyl groups further bearing one or more substituents as set forth above.

As used herein, "arylalkenyl" refers to aryl-substituted alkenyl groups and "substituted arylalkenyl" refers to arylalkenyl groups further bearing one or more substituents as set forth above.

As used herein, "arylalkynyl" refers to aryl-substituted alkynyl groups and "substituted arylalkynyl" refers to arylalkynyl groups further bearing one or more substituents as set forth above.

As used herein, "aroyl" refers to aryl-carbonyl species such as benzoyl and "substituted aroyl" refers to aroyl groups further bearing one or more substituents as set forth above.

The terms heteroalkyl, heteroalkenyl and heteroalkynyl include optionally substituted alkyl, alkenyl and alkynyl structures, as described above, in which one or more skeletal atoms are oxygen, nitrogen, sulfur, or combinations thereof.

The term "heteroaryl" refers to optionally substituted aromatic ring systems having one or more heteroatoms such as, for example, oxygen, nitrogen and sulfur. The term heteroaryl may include five- or six-membered heterocyclic rings, polycyclic heteroaromatic ring systems, and polyheteroaromatic ring systems where the ring system has from two to four, more preferably two to three, and most preferably two, rings. The terms heterocyclic, polycyclic heteroaromatic, and polyheteroaromatic include ring systems containing optionally substituted heteroaromatic rings having more than one heteroatom as described above (e.g., a six membered ring with two nitrogens), including polyheterocyclic ring systems from two to four, more preferably two to three, and most preferably two, rings. The term heteroaryl includes ring systems such as, for example, pyridine, quinoline, furan, thiophene, pyrrole, imidazole and pyrazole.

The term "alkoxy" refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy" refers to an aryl ether radical wherein the term aryl is defined as above. Examples of aryloxy radicals include phenoxy, benzyloxy and the like.

The term "cycloalkyl" refers to cyclic ring-containing groups (e.g., saturated or partially saturated monocyclic, bicyclic or tricyclic alkyl radicals) wherein each cyclic moiety has about 3 to about 8 carbon atoms. Examples of cycloalkyl radicals include cyclopropyl, cyclobutyl, cyclopentyl, cyclohexyl and the like. "Substituted cycloalkyl" refers to cycloalkyl groups further bearing one or more substituents as set forth above.

The term "cycloalkylalkyl" refers to an alkyl radical as defined above which is substituted by a cycloalkyl radical having from about 3 to about 8 carbon atoms.

The term "aralkyl" refers to an alkyl radical as defined above in which one hydrogen atom is replaced by an aryl radical as defined above, such as, for example, benzyl, 2-phenylethyl and the like.

The terms haloalkyl, haloalkenyl and haloalkynyl include alkyl, alkenyl and alkynyl structures, as described above, that are substituted with one or more fluorines, chlorines, bromines or iodines, or with combinations thereof.

As used herein, "heterocyclic" refers to cyclic (i.e., ring-containing) groups containing one or more heteroatoms (e.g., N, O, S, or the like) as part of the ring structure, and having in the range of 3 up to 18 carbon atoms and "substituted heterocyclic" refers to heterocyclic groups further bearing one or more substituents as set forth above.

As used herein, "acyl" refers to alkyl-carbonyl species.

As used herein, "halogen" refers to fluoride, chloride, bromide or iodide atoms.

A wide variety of thermosetting chemistries are contemplated for use as thermosetting resins in the practice of the invention. Such chemistries include, for example epoxies, oxetanes, phenolics, resoles, oxazolines, benzoxazines, monomaleimides, bismaleimides, polymaleimides, cyanate esters, acrylates, methacrylates, maleates, fumarates, itaconates, vinyl esters, vinyl ethers, cyanoacrylates, or styrenics, or combinations thereof.

In certain embodiments, the thermosetting resins are epoxies, oxetanes, phenolics, resoles, oxazolines, benzoxazines, monomaleimides, bismaleimides, polymaleimides, cyanate esters, acrylates, methacrylates, fumarates, vinyl esters, or styrenics, or combinations thereof.

In certain other embodiments, the thermosetting resins are epoxies, monomaleimides, bismaleimides, polymaleimides, cyanate esters or combinations thereof.

In still other embodiments, the thermosetting resins are monomaleimides, bismaleimides, or polymaleimides, or combinations thereof.

While not intending to be limited to a particular theory, the carboxylic acid moiety of the compound of formulae I-VII may help to anchor the anti-bleed agent to metal (e.g. leadframe) surfaces. Accordingly, in some embodiments of the invention, $R_2$ may include additional acidic groups, particularly carboxylic acid side chains.

In other embodiments, $R_2$ may contain one or more vinyl groups. Such compounds of the invention are suitable anti-bleed agents for epoxy cure adhesive compositions, as described below.

In some embodiments, n is 1 to about 100. In other embodiments, n is 1 to about 75. In other embodiments, n is 1 to about 50. In still other embodiments, n is 1 to about 25.

The compounds of the invention are particularly useful in adhesive compositions and pastes for applications in which minimal bleed is required prior to curing, such as for example, in electronics packaging.

Accordingly, the present invention also provides adhesive compositions containing the anti-bleed agents of formulae I-VII. Such compositions include, for example: a thermosetting resin, a quantity of the anti-bleed agent of at least one of formula I-VII sufficient to reduce resin bleed upon application of the adhesive composition to a substrate; and at least one curing initiator.

A reduction in resin bleed may be determined, for example, by application of the adhesive composition with and without the anti-bleed agent between a die and substrate, and visually inspecting the die and substrate following cure of the adhesive composition. Anti-bleed agents of the present invention typically reduce resin bleed by at least about 10%, typically at least about 50%, frequently at least about 80% and often by at least about 100% compared to a control that contains none of the anti-bleed agent of this invention. In certain embodiments, the anti-bleed agents of the present invention reduce resin bleed by at least about 10 fold, at least about 50 fold, at least about 100 fold, or at least about 200 fold.

The invention also provides adhesive compositions containing the anti-bleed agent of formula I or II which are in the form of die-attach pastes. Such compositions can include: a) 2 weight percent to about 98 weight percent (wt %) of a thermosetting resin; b) a quantity of an anti-bleed agent of formula I and/or formula II sufficient to reduce resin bleed upon application of the die-attach paste to a substrate; c) 0 to about 90 wt % of a filler; d) 0.1 wt % to about 5 wt % of at least one curing initiator, based on total weight of the paste; e) 0.1 wt % to about 4 wt %, of at least one coupling agent, based on total weight of the paste.

The at least one curing initiator is typically present in invention adhesive compositions from 0.1 wt % to about 5 wt % based on total weight of the composition, and is typically a free-radical initiator. As used herein, the term "free radical initiator" refers to any chemical species which, upon exposure to sufficient energy (e.g., light, heat, or the like), decomposes into two parts which are uncharged, but which each posses at least one unpaired electron. Preferred free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methyl-propanenitrile), 2,2'-azobis(2-methylbutanenitrile), and 1,1'-azobis(cyclohexanecarbonitrile)), and the like.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include, but are not limited to, silver, nickel, copper, aluminum, palladium, gold, graphite, metal-coated graphite (e.g., nickel-coated graphite, copper-coated graphite, and the like). Examples of suitable thermally conductive fillers which can be employed in the practice of the present invention include graphite, aluminum nitride, silicon carbide, boron nitride, diamond dust, alumina, and the like. Compounds which act primarily to modify rheology include silica, fumed silica, fumed alumina, fumed titanium dioxide, and the like.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In some embodiments, both photoinitiation and thermal initiation may be desirable. For example, curing of a photo-initiator-containing adhesive can be started by UV irradiation, and in a later processing step, curing can be completed by the application of heat to accomplish a free-radical cure. Both UV and thermal initiators may therefore be added to the adhesive composition.

In general, these compositions will cure within a temperature range of 80-220° C., and curing will be effected within a length of time of less than 1 minute to 60 minutes. As will be understood by those skilled in the art, the time and temperature curing profile for each adhesive composition will vary, and different compositions can be designed to provide the curing profile that will be suited to the particular industrial manufacturing process.

In certain embodiments, the adhesive compositions may contain compounds that lend additional flexibility and toughness to the resultant cured adhesive. Such compounds may be any thermoset or thermoplastic material having a Tg of 50° C. or less, and typically will be a polymeric material characterized by free rotation about the chemical bonds, the presence of ether groups, and the absence of ring structures. Suitable such modifiers include polyacrylates, poly(butadiene), poly-THF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of the maleimide and other monofunctional vinyl compound.

Inhibitors for free-radial cure may also be added to the adhesive compositions and die-attach pastes described herein to extend the useful shelf life of compositions containing the imide-extended maleimides. Examples of these inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants include derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

These compositions will perform within the commercially acceptable range for die attach adhesives. Commerically acceptable values for die shear for the adhesives on a 80×80 mil$^2$ silicon die are in the range of greater than or equal to 1 kg at room temperature, and greater than or equal to 0.5 kg at 240° C. Acceptable values for warpage for a 500×500 mil$^2$ die are in the range of less than or equal to 70 Nm at room temperature.

In further embodiments, there are provided methods for reducing resin bleed of a thermosetting resin composition in die-attach applications. Such methods can be performed, for example, by adding to the composition a quantity of an anti-bleed agent of formula I-VII sufficient to reduce resin bleed when the composition is used in die-attach applications.

In certain embodiments, the quantity of anti-bleed agent ranges from 0.1 to about 10 weight percent (wt %) based on total weight of the composition. In some aspects, the anti-bleed is present at an amount less than about 5 weight percent. In other aspects the anti-bleed is present at an amount less than about 1 weight percent. In yet other aspects of the invention, the anti-bleed is present at about 0.001 to about 0.5 weight percent, about 0.05 to about 0.25 weight percent, or at about 0.01 to about 0.15 weight percent.

In still further embodiments of the invention, methods are provided for attaching a die to a substrate, including the steps of: a) applying a thermosetting resin composition to the die or the substrate, wherein the composition includes a quantity of the anti-bleed agent of formula I-VII sufficient to reduce resin bleed upon application of the composition to the die or the substrate, b) contacting the die and the substrate such that the composition is an interface between the die and the substrate, and c) curing the composition, thereby attaching the die to the substrate.

The substrate may be any suitable for use of the die in its intended application. Substrates contemplated for use with invention die attach pastes include, but are not limited to copper lead frames, Alloy 42 lead frames, silicon dice, gallium arsenide dice, germanium dice, and the like.

According to still further embodiments of the invention, methods are provided for attaching a first article to a second article, including the steps of: a) applying an invention adhesive composition to the first article, b) bringing the first and the second article into contact to form an assembly wherein the first article and the second article are separated only by the adhesive composition applied in a), and thereafter, c) curing the invention adhesive composition.

In other embodiments, methods are provided for attaching a first semiconductor die to a second semiconductor die, including the steps of: a) providing a first die having a topside and an underside, b) applying an invention die-attach paste to the underside of the first die, c) juxtaposing the first die and the second die such that the die-attach paste is an interface between the underside of the first die and the topside of the second die, and d) curing the die-attach paste, thereby attaching a first semiconductor die to a second semiconductor die.

Certain anti-bleed agents of the present invention have also been found to increase the increase the viscosity of adhesive compositions, such as die attach pastes, to which they are added. Thus, the present invention also provides methods for increasing the viscosity of adhesive compositions by adding an amount of the anti-bleed agent to an adhesive composition. In one embodiment, the adhesive composition is a die attach paste.

Unexpectedly, the anti-bleed agents of the present invention allow a more repairable bond to be produced. In some applications, a die or other part, may be adhered to a circuit board, and later found to be defective. In such cases, it may be desirable to remove the die or other part and replace it. The anti-bleed agents of formulae I-VII facilitate the ability to remove a die or other part adhered to a substrate and/or repair the bond thereto.

Thus, the present invention also provides methods for removably or repairably adhering a first member, such as a die, to a second member such as a circuit board, by applying an amount of an adhesive composition containing the anti-bleed agent of formula I and/or II to the first and/or second member, contacting the first and second member and curing the adhesive composition. In certain aspects of the invention, the adhesive composition is a die-attach paste. A method for removal of the adhered first and second members of such an assembly is also provided, including the steps of, for example, heating the cured adhesive composition and separating the first and second members. By replacing the removed member with a third member, which may be of the same type as the removed member, the assembly can thus be repaired according to yet another aspect of the invention.

In yet another embodiment of the invention, there are provided assemblies of components adhered together employing the above-described adhesive compositions and/or die attach pastes. The articles may permanently adhered, removably adhered or repairably adhered. For example, assemblies comprising a first article adhered to a second article by a cured aliquot of the above-described adhesive composition are provided. Articles contemplated for assembly employing invention compositions include memory devices, ASIC devices, microprocessors, flash memory devices, and the like.

The anti-bleed agents contemplated for use in the practice of the invention are prepared according to organic chemistry techniques well-known to those skilled in the art.

While this invention has been described with respect to certain embodiments, it should be clear that other modifications and variations would be possible without departing from the spirit of this invention.

EXAMPLES

Example 1

Preparation of Itaconate Acid-Ester (According to Structure I)

A 250 ml, one-neck flask was charged with 11.2 g (0.10 mole) itaconic anhydride and 40.0 g (approximately 0.04 mole) MCR-C12 (Gelest Inc., Morrisville, Pa.). This mixture was stirred at 65° C. for twenty-one hours. The flask was then charged with 100 ml of octane. The octane solution was then filtered over 15 g of silica gel. The octane was removed to yield 40.5 g of a clear colorless liquid. An FTIR was performed on this compound and it was found to have prominent absorptions at 2961, 1746, 1704, 1257, 1017, 790, and 700 wavenumbers.

Example 2

Effects of Anti-Bleed Agents on Resin Bleed

Semiconductor dies were attached to an Au plated ceramic substrate using a thermosetting die-attach paste with or without (control) the anti-bleed agent of the Example 1. The results show the resin bleed before and after oven cure. As seen in FIG. 1, addition of the anti-bleed agent reduced resin bleed during staging and cure.

Example 3

Effects of Anti-Bleed Agents on Resin Bleed

Figure 2:
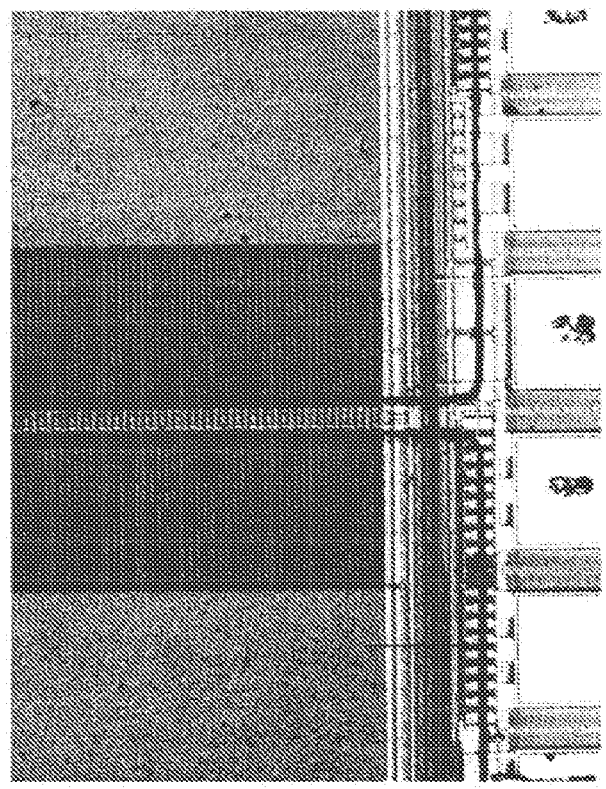
FIG. 2 demonstrates that use of invention compositions and die-attach pastes prevents resin bleed onto wire bond pads.
Figure 2:
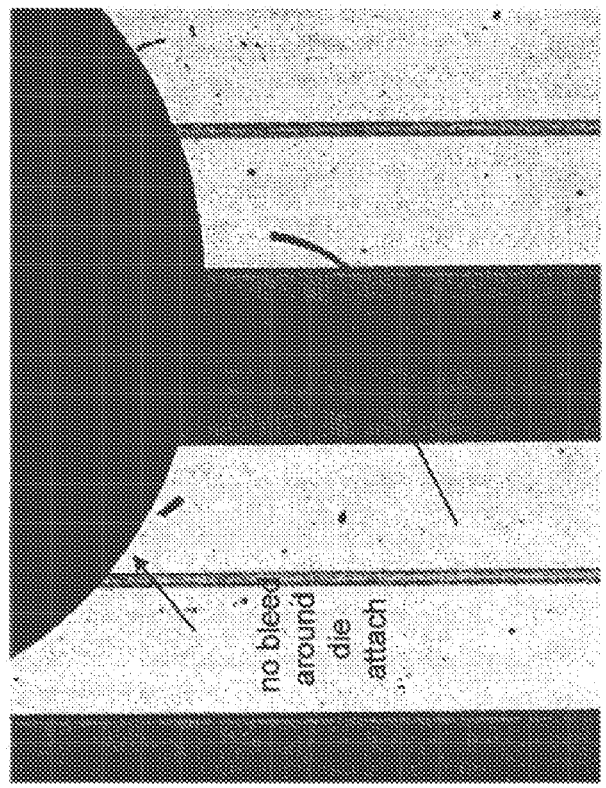

A dot of polyimide thermosetting die-attach paste containing an anti-bleed agent of the invention was applied to a circuit board. The results shown in FIG. 2 illustrate that the resin containing the anti-bleed has not bled onto surrounding areas, such as the open fuse box after 2 hours.

Example 4

Effects of Anti-Bleed Agents on Resin Bleed

Figure 3A:
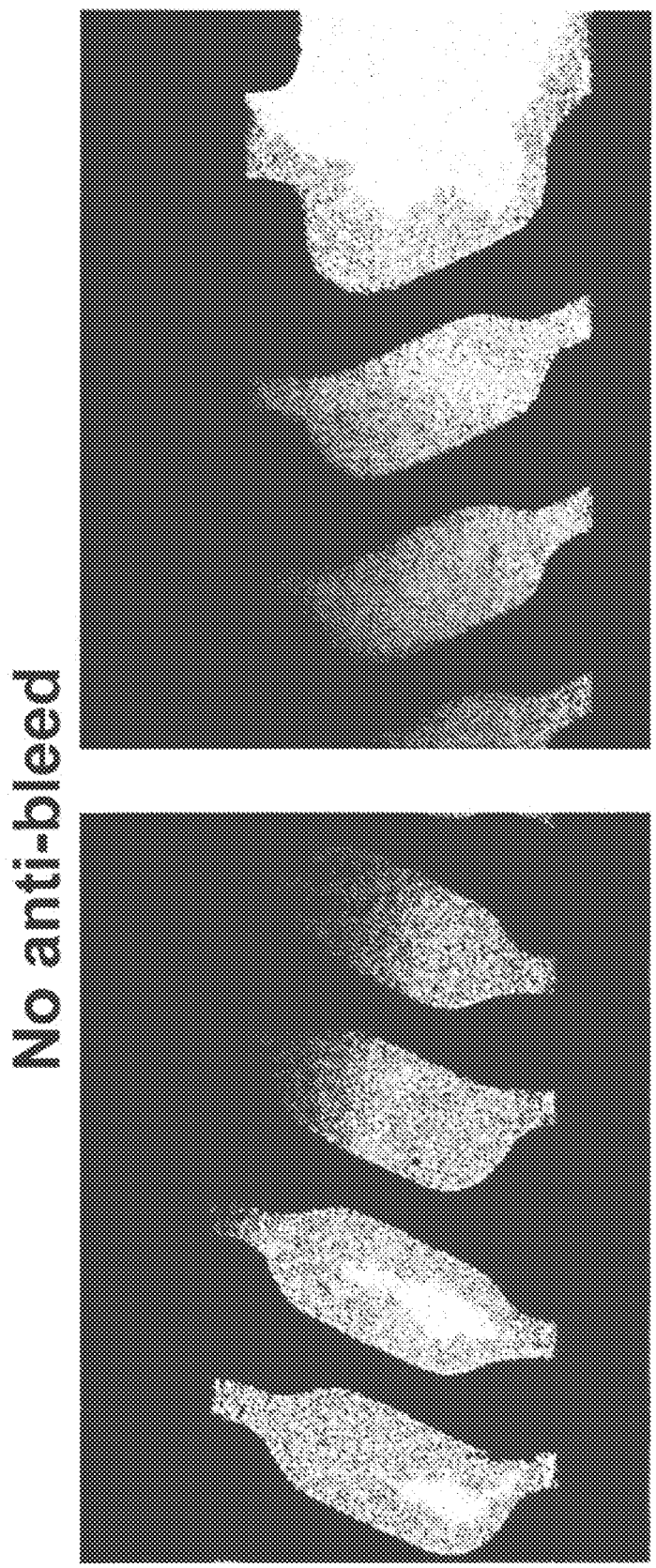
FIGS. 3A-3D shows that use of invention compositions and die-attach pastes prevents resin bleed onto gold plated bond pads using a non-conductive, silica filled paste die-attach paste without (FIG. 3A) an anti-bleed agent of the invention or with increasing amounts of anti-bleed (FIGS. 3B-3D).
Figure 3B:
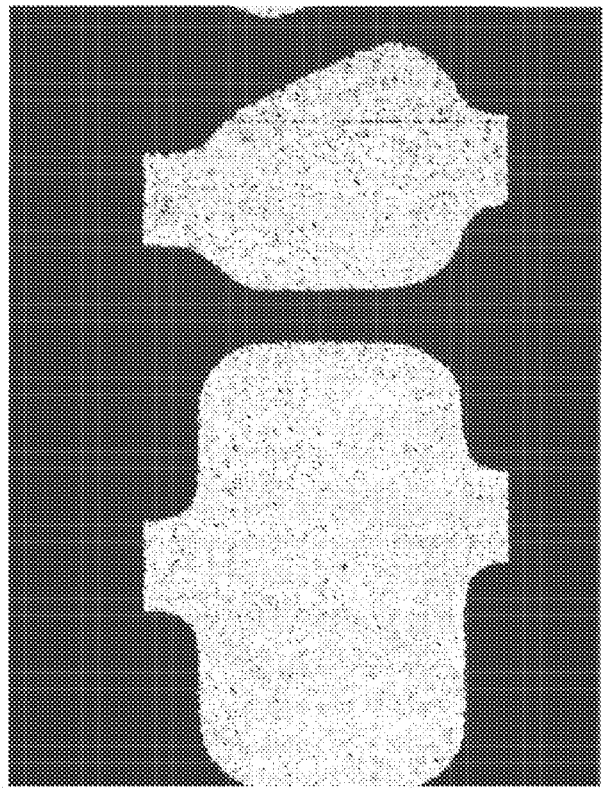
Figure 3B:
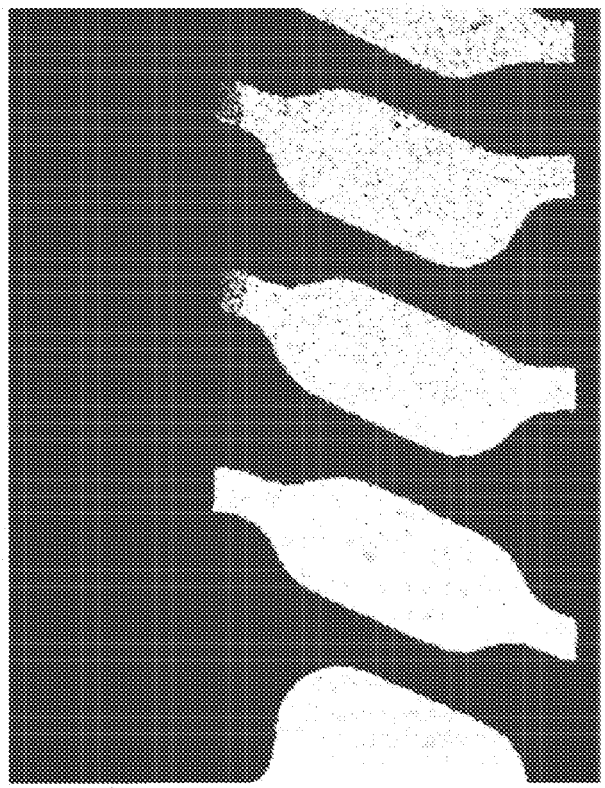
Figure 3C:
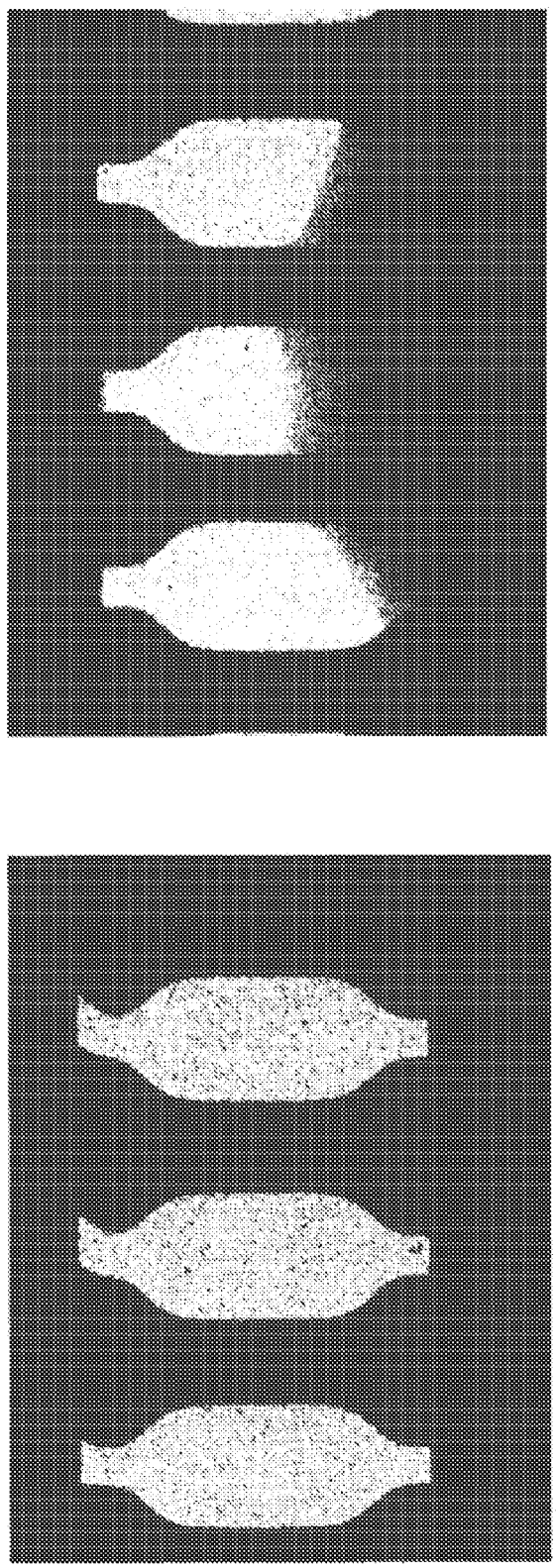
Figure 3D:
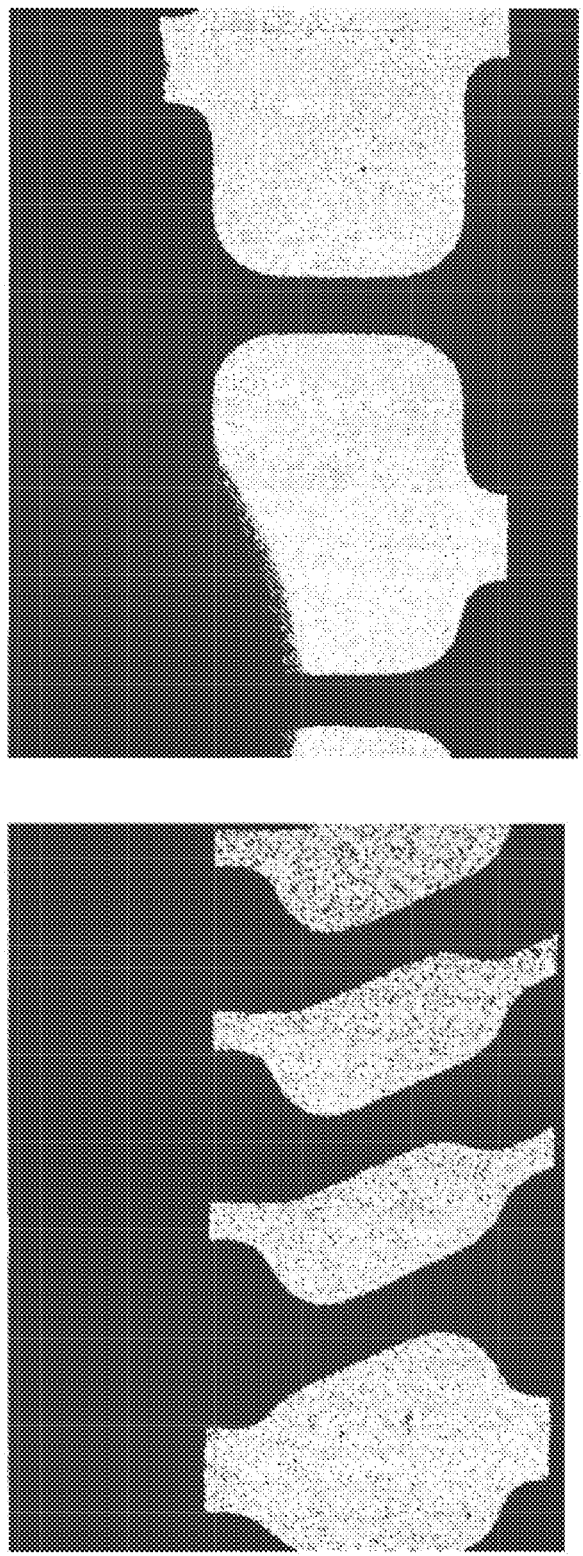

Semiconductor dies were attached to gold plated bond pads using a thermosetting non-conductive, silica filled paste die-attach paste without (FIG. 3A) an anti-bleed agent of the invention or with increasing amounts of anti-bleed (FIGS. 3B-3D). The results show the resin bleed before and after oven cure. The control image (FIG. 3A) shows that the resin almost completely covered the bond pad area. FIGS. 3B-3D show that the anti-bleed eliminated resin migration onto the bond pads. In some cases the paste itself was smeared on the bond pad area, which appears fuzzy in the image.

What is claimed is:

1. A compound selected from the group consisting of compounds III, IV, V and VI, or a salt thereof, having the formulae:

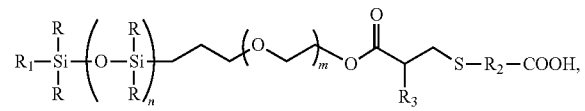

III

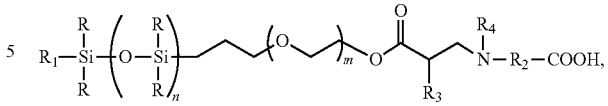

IV

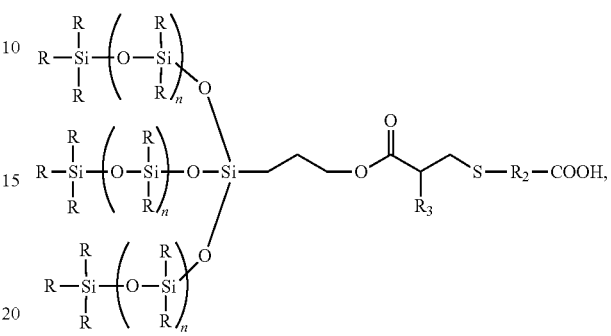

V

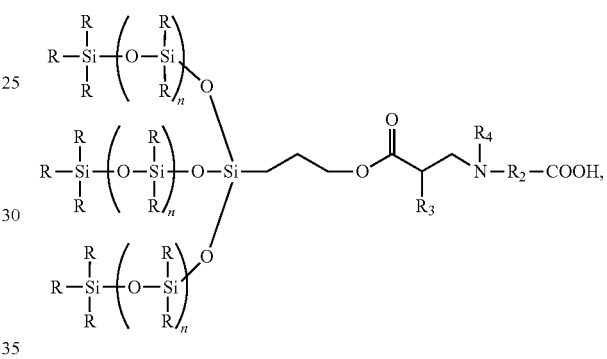

VI wherein:
each of R and $R_1$ is independently selected from the group consisting of a $C_1$-$C_8$ alkyl and phenyl;
$R_2$ is selected from the group consisting of a straight or a branched chain alkylene, a substituted alkylene, an alkenylene, a substituted alkenylene, an alkynylene, a substituted alkynylene, a cycloalkylene, a substituted cycloalkylene, an aromatic, a substituted aromatic, a heterocyclic, a substituted heterocyclic, a heteroaromatic and a substituted heteroaromatic;
$R_3$ is selected from the group consisting of hydrogen and methyl;
$R_4$ is selected from the group consisting of a straight or a branched chain alkyl, a substituted alkyl, an aromatic and a substituted aromatic;
n is an integer having the value between 3 and 500; and
m is an integer having the value between 0 and 100.

2. The compound of claim 1, wherein R is methyl.
3. The compound of claim 1, wherein $R_1$ is butyl.
4. The compound of claim 1, wherein R is methyl and $R_1$ is butyl.
5. The compound of claim 1, wherein $R_2$ is selected from the group consisting of an optionally substituted methylene, ethylene, ethenylene, methylethenylene, n-propylene, isopropylene, propenylene, butylene, isobutylene, sec-butylene, tert-butylene, butenylene, pentylene, pentenylene, hexylene, hexenylene, octylene, octenylene, ethylallylene, ethyloctenylene, ethyldodecenylene, ethyloctadecenylene, cyclohexanylene, cyclohexenylene, bicyclohexenylene, norbornenylene, phenylene and naphthylene.

6. A compound selected from the group consisting of compounds III, IV, V and VI, or a salt thereof, having the formulae:

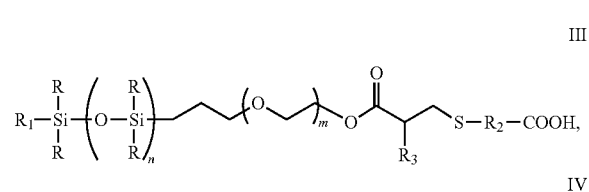

III

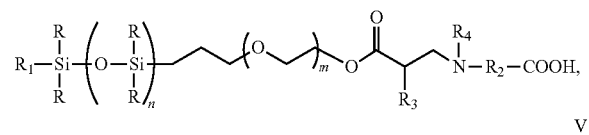

IV

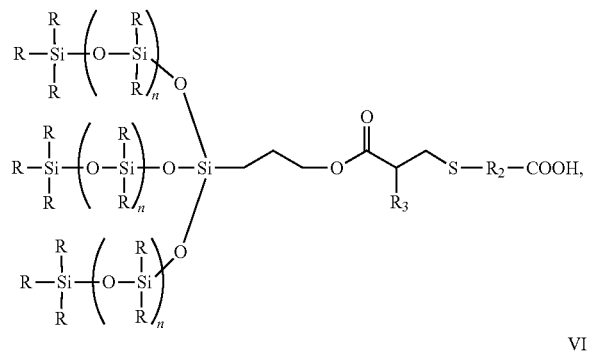

V

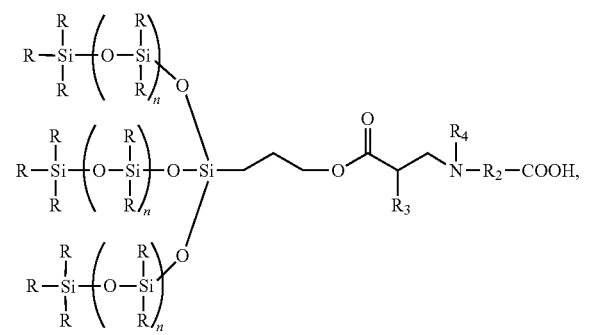

VI wherein:
each of R and $R_1$ is independently selected from the group consisting of a $C_1$-$C_8$ alkyl and phenyl;
$R_2$ has the formula $(CH_2)_{m-1}$-$CH_2$-$R_5$-$R_6$;
$R_3$ is selected from the group consisting of hydrogen and methyl;
$R_4$ is selected from the group consisting of a straight or a branched chain alkyl, a substituted alkyl, an aromatic and a substituted aromatic;
$R_5$ is a heteroatom;
$R_6$ is an optionally substituted alkyl;
n is an integer having the value between 3 and 500; and
m is an integer having the value between 1 and 12.

7. The compound of claim 1, wherein $R_2$ is selected from the group consisting of an optionally substituted methylene, ethylene, ethenylene, n-propylene, isopropylene, propenylene, butylene, isobutylene, sec-butylene, tert- butylene, butenylene, pentylene, pentenylene, hexylene, hexenylene, octylene and octenylene.

8. The compound of claim 1, wherein $R_2$ is selected from the group consisting of maleimide, cyclohexanylene, cyclohexenylene, bicyclohexenylene and benzoic acid.

9. A compound selected from the group consisting of compounds III, IV, V and VI, or a salt thereof, having the formulae:

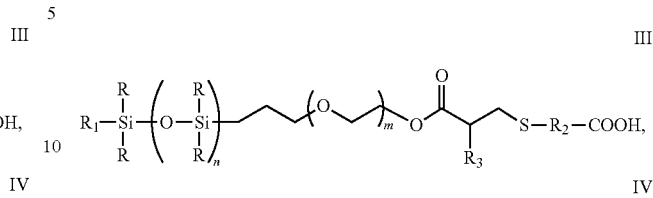

III

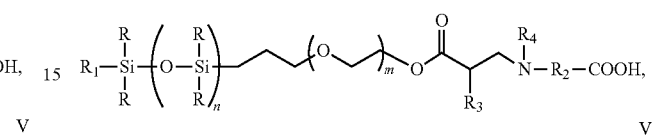

IV

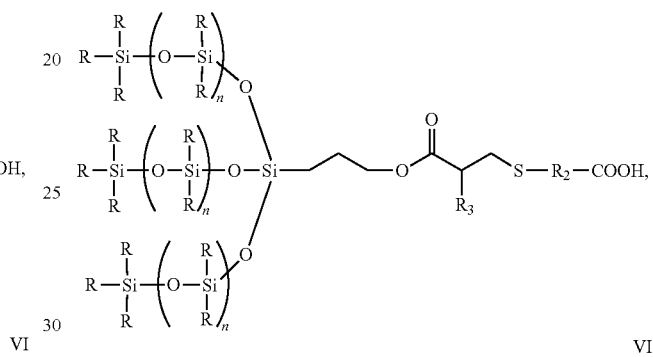

V

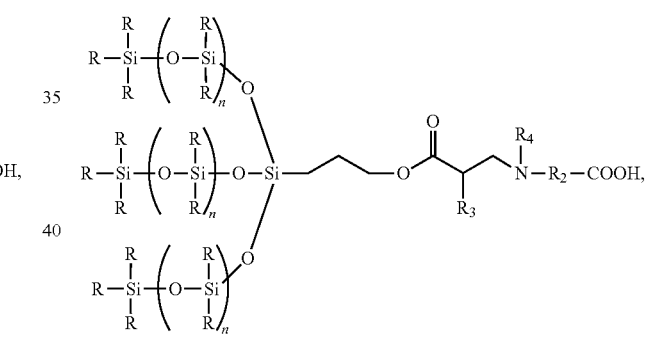

VI wherein:
each of R and $R_1$ is independently selected from the group consisting of a $C_1$-$C_8$ alkyl and phenyl;
$R_2$ has the formula $(CH_2)_{m-1}$-$Ch_2$-$R_4$-$R_5$;
$R_3$ is selected from the group consisting of hydrogen and methyl;
$R_4$ is a heteroatom;
$R_5$ is an optionally substituted alkyl; and
each m independently has the value between 1 and 12.

10. The compound of claim 1, wherein
$R_2$ is selected from the group consisting of a $C_4$-$C_{12}$ straight or branched chain alkylene, a substituted alkylene, an alkenylene, a substituted alkenylene, an alkynylene, a substituted alkynylene, a cycloalkylene, a substituted cycloalkylene, a heterocyclic, a substituted heterocyclic, a heteroaromatic and a substituted heteroaromatic; and n has the value between about 10 and about 250.

11. The compound of claim 1, wherein $R_2$ comprises at least one vinyl moiety.

12. A compound selected from the group consisting of:
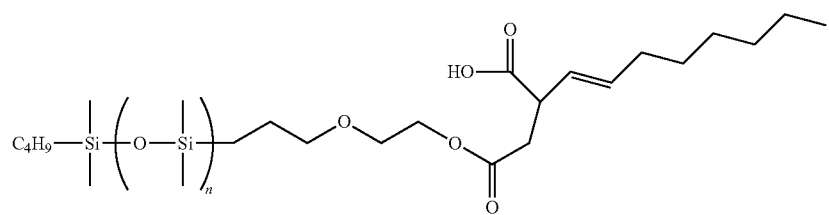
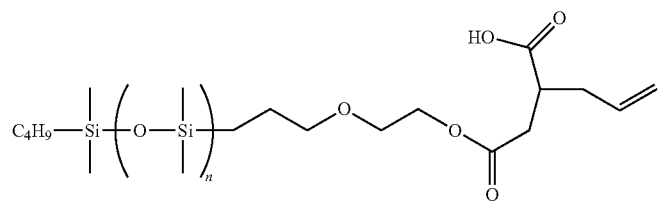
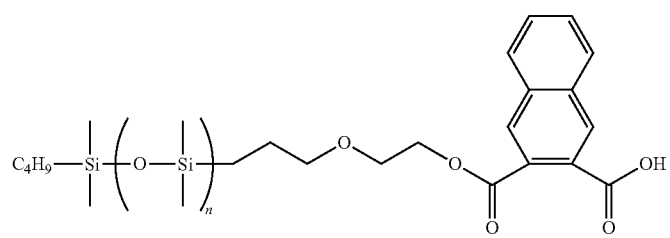
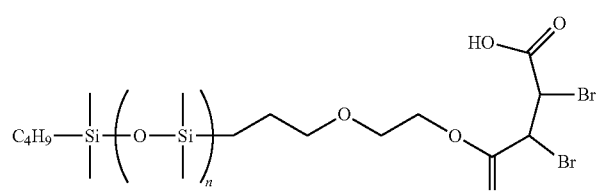
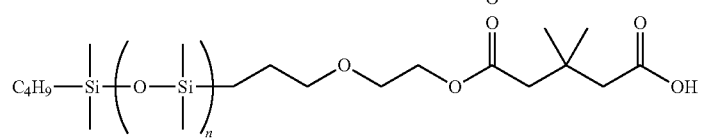
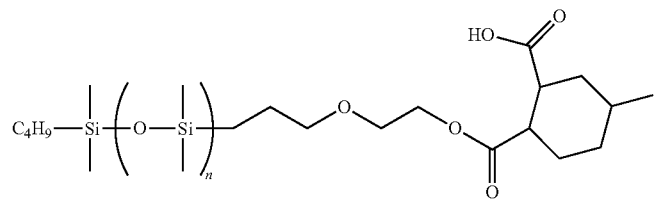
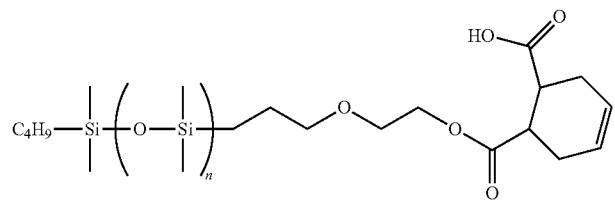
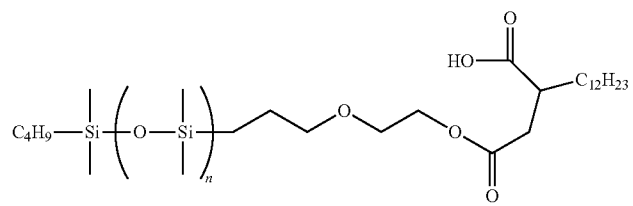

-continued

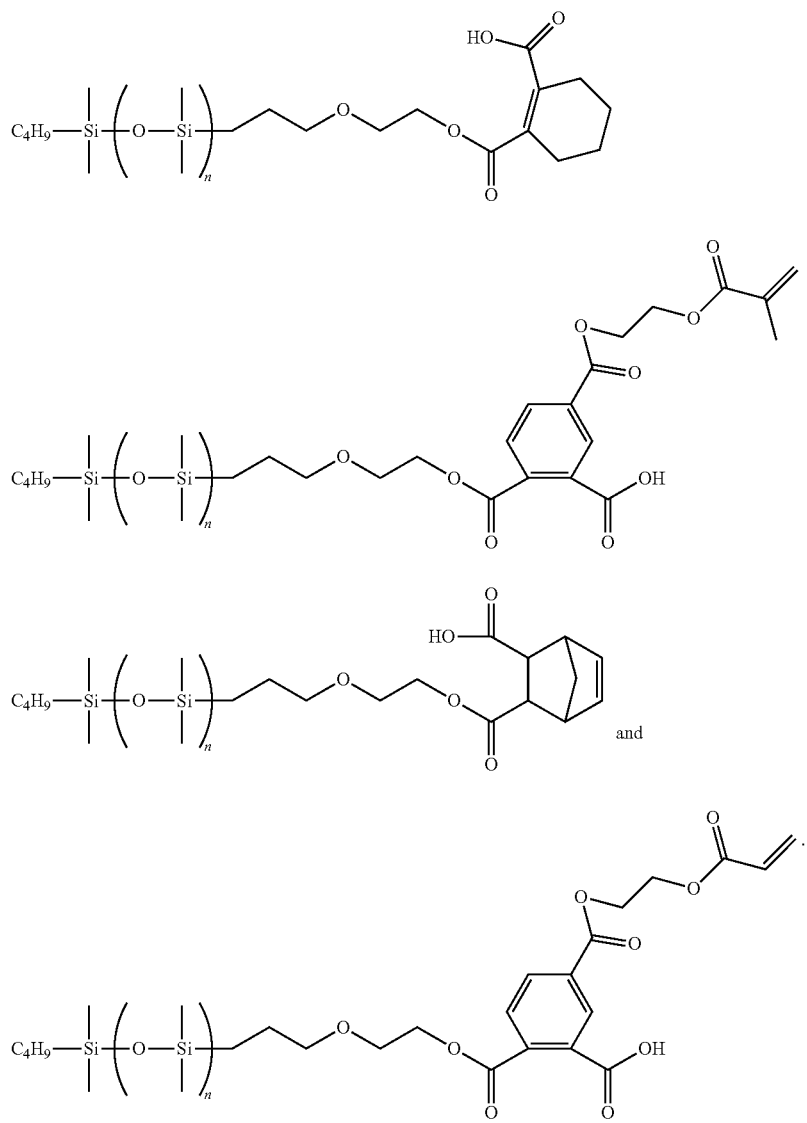

13. A compound having the formula:

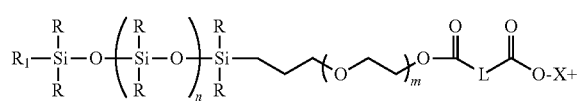

wherein

X is a cation selected from the group consisting of ammonium, alkyl ammonium, dialkyl ammonium, tetraalkyl ammonium, cycloalkyl ammonium, aryl ammonium, substituted aryl ammonium, pyridinium, or a mono-valent or poly-valent metal cation selected from lithium, sodium, potassium, cesium, magnesium, calcium, strontium, barium, copper, zinc, aluminum, tin and bismuth; and L is selected from the group consisting of a $C_2$-$C_{10}$ alkylene, alkenylene, cycloalkylene, cycloalkenylene, arylene and naphthylene.

14. A compound selected from the group consisting of:

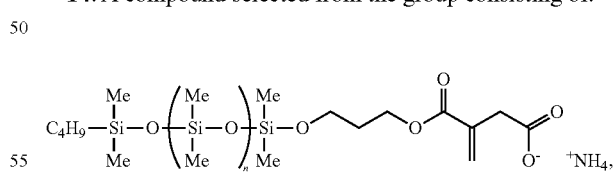

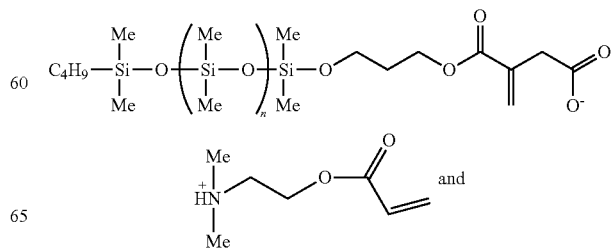

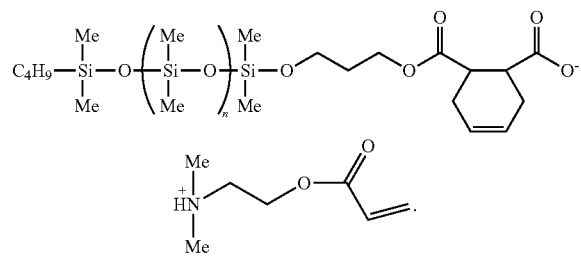

15. A method for reducing resin bleed, comprising:
(1) providing a thermosetting resin, an anti-bleed agent and an at least one curing initiator; and
(2) preparing an adhesive composition by combining:
   (a) a quantity of the thermosetting resin;
   (b) a quantity of the anti-bleed agent sufficient to reduce resin bleed upon application of the adhesive composition to a substrate; and ;
   (c) a quantity of the at least one curing initiator,
wherein the anti-bleed agent is a compound is selected from the group consisting of compounds I, II, III, IV, V and VI, or a salt thereof, having the formulas:

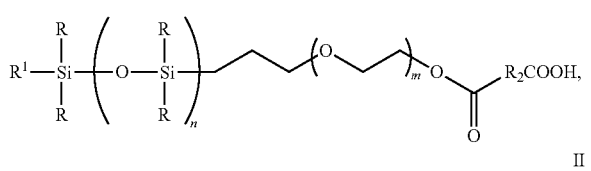

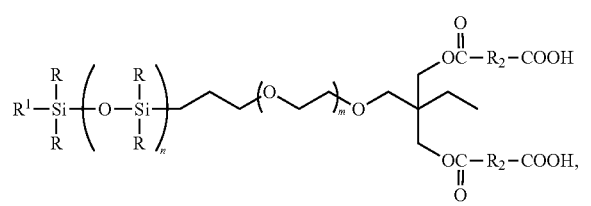

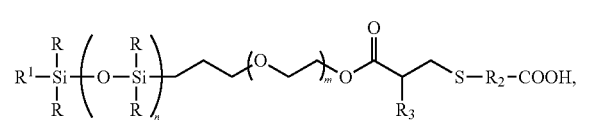

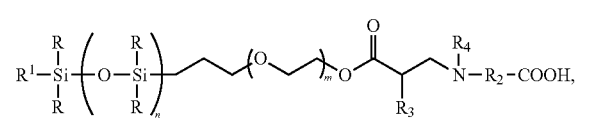

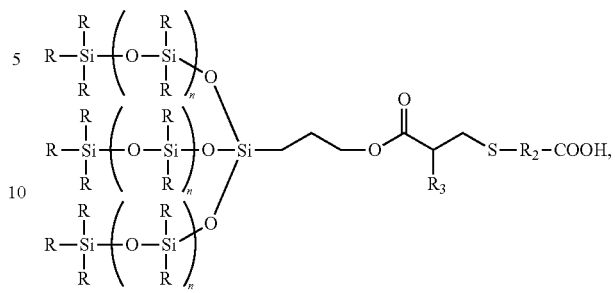

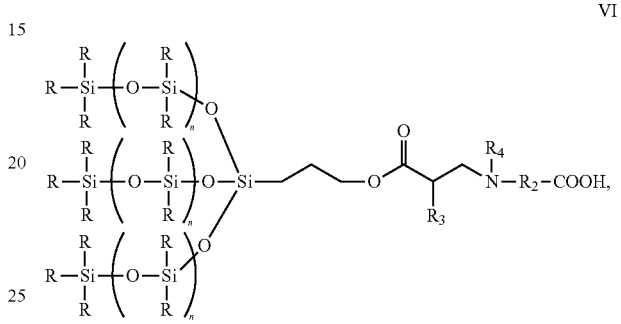

wherein:
each of R and $R_1$ is independently selected from the group consisting of a $C_1$-$C_8$ alkyl and phenyl;
$R_2$ is selected from the group consisting of a straight or a branched chain alkylene, a substituted alkylene, an alkenylene, a substituted alkenylene, an alkynylene, a substituted alkynylene, a cycloalkylene, a substituted cycloalkylene, an aromatic, a substituted aromatic, a heterocyclic, a substituted heterocyclic, a heteroaromatic and a substituted heteroaromatic;
$R_3$ is selected from the group consisting of hydrogen and methyl;
$R_4$ is selected from the group consisting of a straight or a branched chain alkyl, a substituted alkyl, an aromatic and a substituted aromatic;
n is an integer having the value between 3 and 500; and
m is an integer having the value between 0 and 100,
to thereby achieve the reduction of resin bleed when the adhesive composition is applied to a substrate as a die-attach paste.

16. The method of claim 15, wherein the thermosetting resin is selected from the group consisting of epoxies, phenolics, phenolic novalacs, cresolic novalacs, polyurethanes, oxetanes, oxazolines, benzoxazines, resoles, maleimides, polyimides, monomaleimides, bismaleimides, polymaleimides, cyanate esters, polyvinyl alcohols, polyesters, polyureas, acrylics, acrylates, polyamides, polyacrylates, methacrylates, maleates, fumarates, itaconates, vinyl esters, vinyl ethers, polysiloxanes, cyanoacrylates, styrenics and combinations thereof.

17. The method of claim 15, wherein the anti-bleed agent comprises between about 0.01 and about 5.0 weight percent of the adhesive composition.

* * * * *